US007994485B2

(12) United States Patent
Feke et al.

(10) Patent No.: US 7,994,485 B2
(45) Date of Patent: Aug. 9, 2011

(54) APPARATUS AND METHOD FOR FLUORESCENCE MEASUREMENTS USING SPATIALLY STRUCTURED ILLUMINATION

(75) Inventors: Gilbert Feke, Durham, CT (US); Laurie L. Voci, Victor, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 12/556,662

(22) Filed: Sep. 10, 2009

(65) Prior Publication Data

US 2010/0038559 A1 Feb. 18, 2010

Related U.S. Application Data

(63) Continuation-in-part of application No. 12/411,432, filed on Mar. 26, 2009.

(60) Provisional application No. 61/043,188, filed on Apr. 8, 2008.

(51) Int. Cl.
*G01N 21/64* (2006.01)

(52) U.S. Cl. ................................... 250/458.1

(58) Field of Classification Search ................ 250/458.1
See application file for complete search history.

(56) References Cited

U.S. PATENT DOCUMENTS

| 4,343,782 A | 8/1982 | Shapiro |
| 4,835,103 A | 5/1989 | Cercek et al. |
| 5,096,807 A | 3/1992 | Leaback |
| 5,355,215 A | 10/1994 | Schroeder et al. |
| 5,933,232 A | 8/1999 | Atzler et al. |
| 6,376,818 B1 | 4/2002 | Wilson et al. |
| 6,420,183 B1 | 7/2002 | Krahn et al. |
| 6,985,225 B2 | 1/2006 | Bechem et al. |
| 6,994,747 B2* | 2/2006 | Hiraiwa et al. ............ 117/13 |
| 7,199,377 B2 | 4/2007 | Wulf et al. |
| 2003/0010930 A1* | 1/2003 | Thorwirth ............ 250/458.1 |
| 2003/0165021 A1* | 9/2003 | Kawasaki ............ 359/690 |
| 2005/0218338 A1* | 10/2005 | Wulf et al. ............ 250/458.1 |
| 2006/0029523 A1* | 2/2006 | Tanaami ............ 422/82.08 |
| 2006/0098895 A1 | 5/2006 | Westphal |
| 2006/0184043 A1* | 8/2006 | Tromberg et al. ............ 600/476 |

FOREIGN PATENT DOCUMENTS

| DE | 197 20 667 | 4/1997 |
| DE | 199 30 816 | 4/2001 |
| WO | WO 90/15317 | 12/1990 |

OTHER PUBLICATIONS

Fournel et al., "Stereoscopic particle image velocimetry using telecentric lenses," 2003, Measurement Science and Technology, vol. 14, pp. 494-499.*

* cited by examiner

*Primary Examiner* — David P Porta
*Assistant Examiner* — Kiho Kim

(57) ABSTRACT

An apparatus and method for depth selected fluorescence measurements is provided. The apparatus may include a carrier for at least one sample substance; projection optics; an image capture module; a signal processor to transform the data image to provide depth selected fluorescence measurement for the at least one sample substance. The apparatus is arranged such that a first optical axis is inclined relative to a second optical axis so that the projection optics have an angle of inclination relative to the image plane. The angle of inclination is selected so that a component of excitation radiation incident upon, but not absorbed by, the at least one sample substance is scattered or reflected to reduce excitation radiation from reaching the detection beam path.

14 Claims, 22 Drawing Sheets

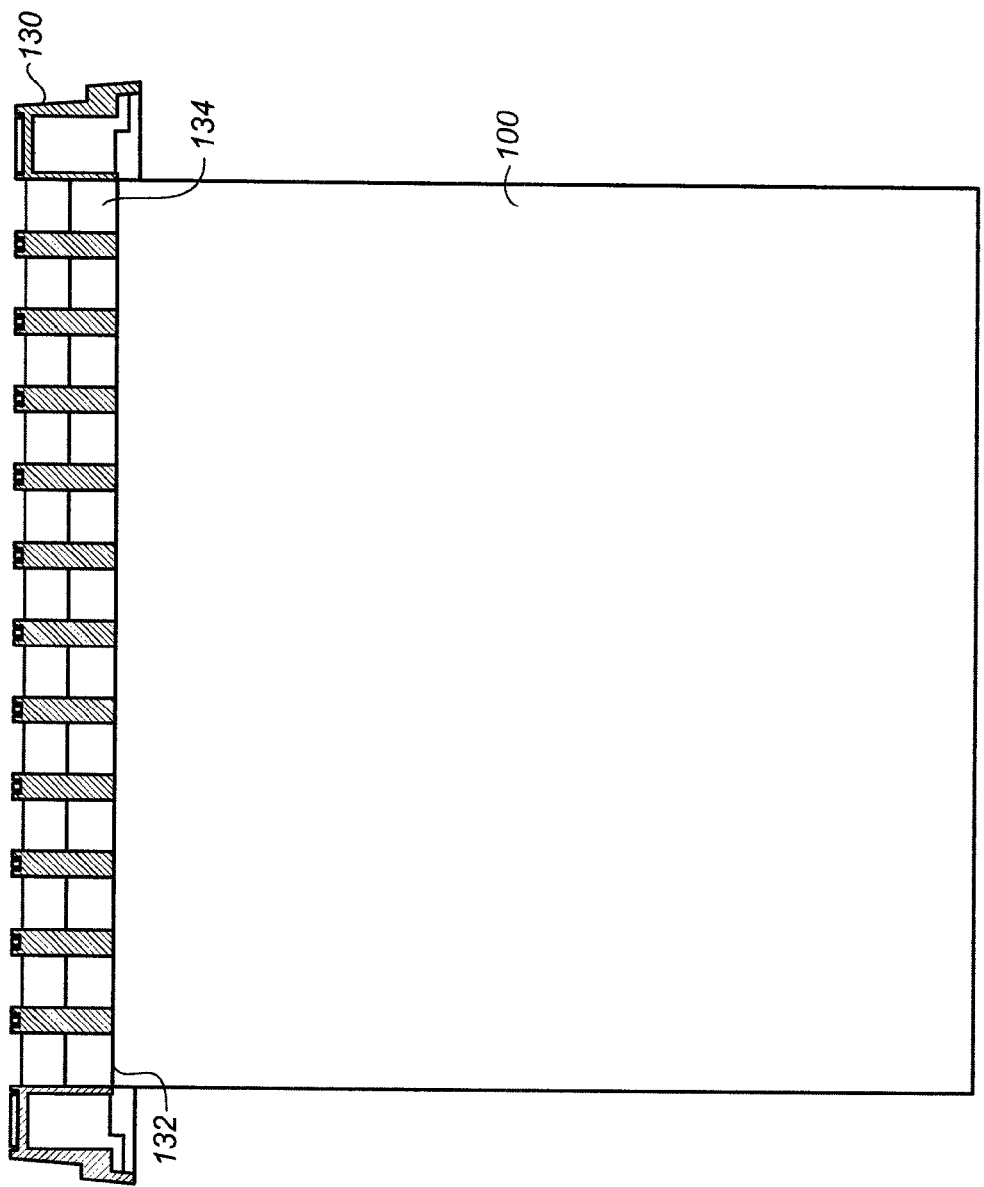

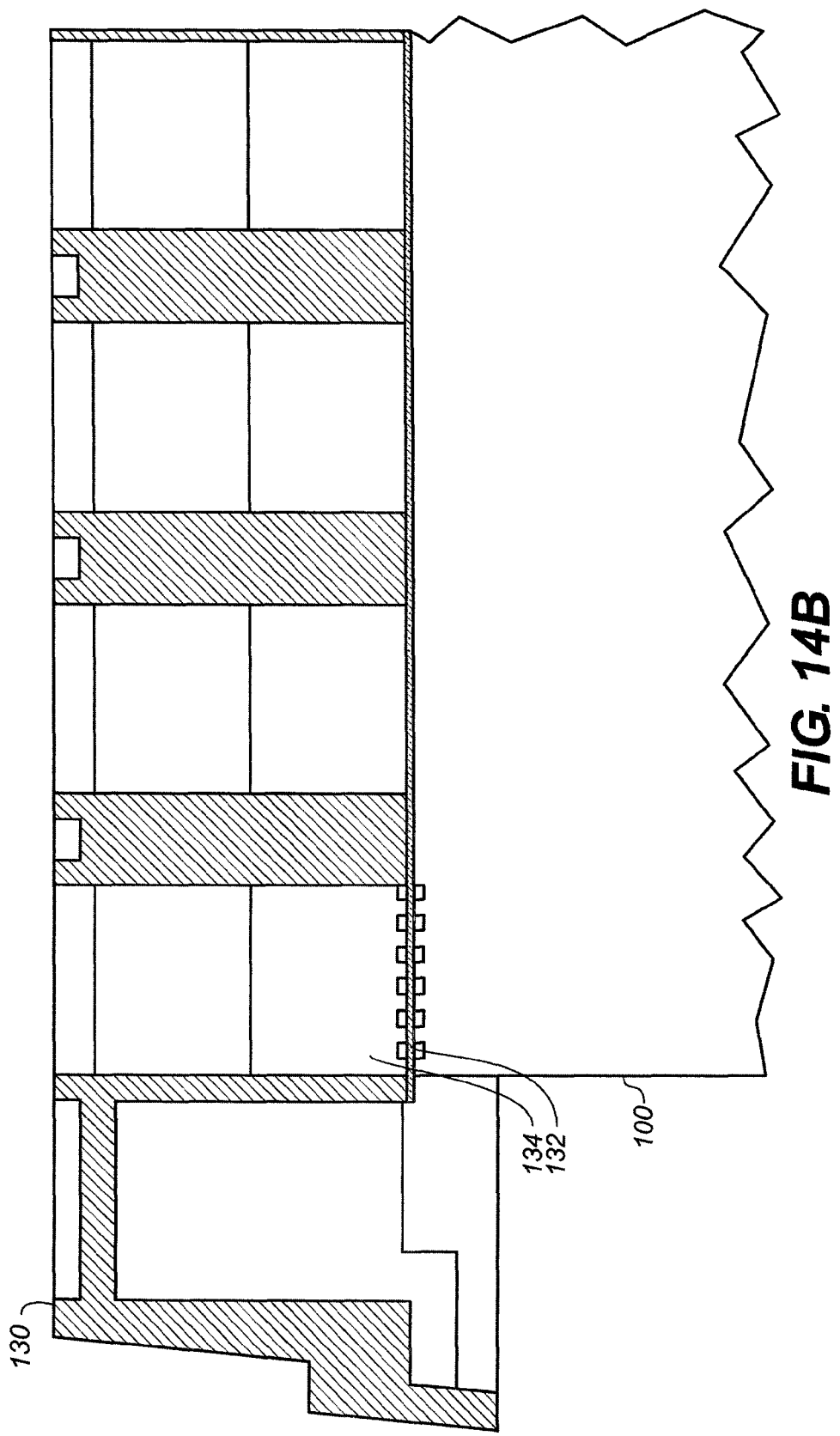

APPARATUS AND METHOD FOR FLUORESCENCE MEASUREMENTS USING SPATIALLY STRUCTURED ILLUMINATION

CROSS REFERENCE TO RELATED APPLICATION

This application is a continuation-in-part of copending, commonly assigned U.S. patent application Ser. No. 12/411,432 filed Mar. 26, 2009 by Feke et al and entitled Apparatus and Method for Fluorescence Imaging and Tomography Using Spatially Structured Illumination, the entire disclosure of which is incorporated by reference into this specification, which claims priority from U.S. Provisional Application No. 61/043,188, entitled "Apparatus and Method for Fluorescence Imaging and Tomography Using Spatially Structured Illumination" by Feke et al., filed on Apr. 8, 2008, incorporated herein by reference.

FIELD OF THE INVENTION

The invention relates generally to the field of fluorescence measurement systems. More specifically, the invention relates to an apparatus for fluorescence measurements using spatially structured illumination.

BACKGROUND OF THE INVENTION

State of the art fluorescence measurement techniques enable detection and analysis of samples of one or more substances in a contact-free manner. Various known fluorescence measurement techniques include labeling the substances with one or more selected fluorescent dyes, or employing the intrinsic fluorescence of the substances. For analyses of this type, samples of the substances are illuminated with exciting radiation or light of wavelengths or wavelength regions which are suited to the absorption behavior of the intrinsic fluorescence or the fluorescent dyes used (usually the absorption maxima). The response of the intrinsic fluorescence or fluorescent dyes is to emit light characteristic for the intrinsic fluorescence or fluorescent dyes, whose wavelength is usually longer than that of the exciting radiation or light. Hence, it is possible to measure quantitatively changes in the physical property, for example concentration of the substance in a solution, composition, physical environment, and similar parameters, via changes in the fluorescence behavior, for example changes in the fluorescence intensity and/or in the wavelength of the absorption and/or emission.

In one particular known class of fluorescence measurement or analyses called adherent cell assays, adherent cells of various tissue types are grown in culture and incubated in a growth medium. A first known subclass of adherent cell assays requires that the growth medium include a fluorescent dye. The cells will absorb the dye at particular rates, and these rates may be correlated with various physiological functions of the cells such as $K^+$ channel activity. A cell which has absorbed dye will typically fluoresce at an enhanced intensity as compared to the growth medium which incorporates that dye. Fluorescence measurements or analyses of this type are of significant importance in the pharmaceutical industry since they may be employed to screen a variety of tissue types for interaction with chemical species of pharmaceutical interest. In an analysis of this type, adherent cells may be cultured in a tissue culture dish, or alternatively in a tissue culture treated microtiter plate which includes a plurality of wells.

FIGS. 1A and 1B show an example of a known type of 96 well microtiter plate or carrier 130. In this case, each of the microtiter plate wells has a substantially planar, optically transparent bottom wall or member 132, such as a plastic film or a quartz plate. Tissue cells are cultured in a layer on the upper surface of the bottom member with a supernatant layer of growth medium thereabove. Chemical species being assayed are placed into the supernatant liquid together with a fluorescent dye. Then, the effect of the chemical species on cell metabolism is assayed by measuring the fluorescence of the cell layers. Such techniques are well known in the art and are described, for example, in U.S. Pat. Nos. 4,343,782, 4,835,103 and PCT published application WO 90/15317. In order to measure the fluorescence of the cells, the cell layers are illuminated with light of a first wavelength and emission at a second wavelength is monitored by a photodetector device, for example a camera. Problems may arise in this type of an assay because the cell layer is typically on the order of 10 microns in thickness, while the depth of the supernatant liquid is on the order of many millimeters. While the relative intensity of the emission from the supernatant liquid is generally lower than that from the cells which have absorbed the dye, fluorescence from the supernatant liquid may constitute a significant source of error in these assays because of the large relative volume of the supernatant in the fluorescence detection volume.

A second known subclass of adherent cell assays is like the first subclass except that instead of the supernatant layer of growth medium including a fluorescent dye, the cells are intrinsically fluorescent by virtue of their expression of a fluorescent genetic reporter such as green fluorescent protein. Although the supernatant layer in this case typically does not contain a fluorescent dye, the autofluorescence of the supernatant layer may constitute a significant source of error in these assays because of the large relative volume of the supernatant in the fluorescence detection volume.

In another particular known class of fluorescence analyses called homogeneous fluorescence assays, all the components of the assay are present during measurement. The reactions occur in solution generally without a solid-phase attachment. Problems may arise in this type of an assay because of variability in the contents among a plurality of containers of the solution, for example the plurality of wells in a microtiter plate, wherein the variable factors may include the total volume of solution in each well, attenuation of both the excitation and emission radiation in the solution, and surface tension, all potentially affecting the intensity and wavelengths of the volume-integrated fluorescence measured in each container.

A known subclass of homogeneous fluorescence assays comprises fluorescence polarization assays, which involve polarization sensitive detection of fluorescent emission in response to polarized excitation. In addition to the problems related to homogeneous fluorescence assays described above, fluorescence polarization assays may further be prone to problems relating to scattering-induced depolarization when the solution is turbid.

Standard microtiter plates have a base of approximately 128 mm×86 mm in versions with 96, 384 or 1,536 wells. A known automated standard method is the analysis of a microtiter plate with the aid of commercial microtiter plate readers having a fixed geometry for measuring excitation and emission of the fluorescent dye. For an extensive and complete analysis, the microtiter plate is transported electromechanically and sequentially, well-by-well, into the excitation/measurement position. There exist measuring systems with different illuminating geometries for perpendicular excitation from above or below and measuring the fluorescence from above or, through the transparent base of microtiter plates, from below, as is described, for example, in DE 197 20 667 A1 and corresponding U.S. Pat. No. 5,933,232. Since high-throughput screening for drug research requires several millions of chemical substances to be tested for their action in as short a time as possible, a high rate of measurement is a prerequisite for this high throughput. In the case of conventional fluorescence readers, moving the plate mechanically stands in the way of this. The measurement times for a microtiter plate with 1,536 wells which have to be addressed individually are in the minute range.

U.S. Pat. No. 5,096,807 discloses an image-based or imaging immunoassay detection apparatus system and method capable of imaging multiple light emitting reactions from small volume samples simultaneously and quantifying the same. Although imaging is obviously advantageous with regard to the prerequisite for high throughput, the illumination and detection geometry of conventional fluorescence-measuring systems, whether sequential or simultaneous using imaging methods, in which the sample is excited perpendicularly from below or from above and the fluorescence is detected likewise perpendicularly from below or from above, proves to be very disadvantageous for both adherent cell assays and homogeneous fluorescence assays for the reasons described above. Furthermore, because the path of the excitation light and emission light is unitary in the geometry of conventional fluorescence-measuring systems, transmission or reflection of the excitation light into the optical path of fluorescence detection may further limit quantitation of fluorescence measurements due to background caused by spectral leakage, or otherwise cause high expense with regard to spectral filtering technology.

The problem of interfering background fluorescence for adherent cell assays is addressed in U.S. Pat. No. 6,420,183, where an absorption dye is added to the supernatant solution to eliminate the exciting beam and the emitted radiation in the supernatant liquid over the cell layer to be observed. However, the use of absorbent dyes is also problematic because, on the one hand, their biochemical reaction is unclear and, on the other hand, the absorption in the supernatant liquid is incomplete and can ultimately also have an undesirable effect in the cell layer.

U.S. Pat. No. 5,355,215 discloses an instrument that specifically reduces the unwanted background fluorescence of the supernatant liquid and accordingly improves the wanted signal from a cell layer at the transparent base of the wells. The excitation light impinges on the base of the microtiter plate at an oblique incident angle from below and, in addition, the excitation light bundle cross section per well is limited through a multi-pinhole diaphragm in order to observe the fluorescent radiation, as far as possible, only from a small section volume at the base of each well. As a general condition, an optical illumination axis or detection axis is directed at an angle to the normal direction of the microplate. However, due to divergence of the excitation illumination, the excited liquid volume in the wells is dependent upon position.

FIGS. 2A, 2B, and 3 show an example of position dependence of the excited liquid volume. FIGS. 2A and 2B show microtiter plate 130 in cross-section. Excitation radiation path 110 is divergent and illuminates the fluorescent sample substances in wells A-H. FIG. 3 shows the relative variation of the excited volume of the fluorescent sample substances within each well, with the greatest excited volume corresponding to well H, the well closest to the radiation source. The detected fluorescence signal is typically proportional to the excited volume, so the variation in the excited volume directly corresponds to a variation in the detected fluorescence signal. This analysis assumes that the volumes of the substances within the wells are sufficiently large so that any variation in the volume or surface tension is inconsequential.

U.S. Pat. No. 6,985,225 discloses a fluorescence measurement system wherein the arrangement for fluorescence excitation contains a two-dimensionally extended sample-receiving device and at least two illumination sources for exciting the fluorescence of the samples. The illumination sources are extended linearly and arranged in such a way that the illuminated area of the sample-receiving device is, as far as possible, homogeneously illuminated directly or via deflecting mirrors at an opening angle of ≦30°. A detector system for the fluorescence light from the sample-receiving device is arranged on either side of the sample-receiving device in such a way that it detects fluorescence emission from the area of measurement at an angle outside the range of reflection of the excitation light of the illumination sources at the illuminated area of the sample-receiving device, preferably at an angle in the range from 80° to 100°, particularly preferably about 90°, to the extended plane of the area of the sample-receiving device. However, due to divergence of the illumination, the excited liquid volume in the wells is dependent upon position. Furthermore, the fluorescence detection volume is not limited to a small section at the base of the sample container, for example a tissue culture dish or each well of a microtiter plate.

FIGS. 4 and 5 show an example of position dependence of the excited liquid volume for the case of two excitation radiation sources. FIG. 4 shows microtiter plate 130 in cross-section. Excitation radiation paths 110 and 111 are divergent and illuminate the fluorescent sample substances in wells A-H. FIG. 5 shows the relative variation of the excited volume of the fluorescent sample substances within each well, with the greatest excited volumes corresponding to wells A and H, the wells closest to the radiation sources. The detected fluorescence signal is typically proportional to the excited volume, so the variation in the excited volume directly corresponds to a variation in the detected fluorescence signal. This analysis assumes that the volumes of the substances within the wells are sufficiently large so that any variation in the volume or surface tension is inconsequential.

U.S. Pat. No. 7,199,377 discloses a device for optical analytic measurement in a multisample carrier, wherein, during excitation of all of the wells, the fluorescence radiation of each well is measured simultaneously without, as far as possible, impermissible contributions of background radiation which falsify the characteristic emission of the sample material. The excitation light is directed from a light source on the multisample carrier coaxially in a ring-shaped manner around an optical axis wherein the optical axis is oriented in direction of a surface normal of the multisample carrier and coaxial to the direction of the readout beam path. A ring mirror unit with at least one curved ring mirror is arranged coaxial to the optical axis in such a way that the excitation light illuminates the multisample carrier homogeneously, as far as possible, on all sides at an oblique incident angle. However, due to divergence of the excitation illumination, the excited liquid volume in the wells is dependent upon position. Furthermore, the fluorescence detection volume is not limited to a small section at the base of the sample container, for example a tissue culture dish or each well of a microtiter plate.

US Publication 2003/0010930 discloses an arrangement for reading out the fluorescence radiation of specimen carriers with a plurality of individual specimens. For purposes of exciting fluorescence radiation in selected individual specimens, a switchable electro-optical matrix is provided for generating illumination which is limited in a spatially defined manner. An arrangement is disclosed for reading out the fluorescence radiation of selected individual specimens of multispecimen carriers having a switchable electro-optical matrix for generating illumination which is limited in a spatially defined manner. An optical system images the electro-optical matrix on the specimen carrier, and a high-sensitivity photoreceiver provides integral measurement of the fluorescence radiation of the excited individual specimens of the specimen carrier. A spatially differentiated illumination of a specimen carrier with a plurality of specimens is disclosed using an electro-optical matrix which minimizes the proportion of excitation radiation contributing to the fluorescence signal in high-resolution imaging. The electro-optical matrix and the specimen carrier are inclined relative to the optical axis of the optical system and are subject to a Scheimpflug condition. The angles of inclination of the electro-optical matrix and of the specimen carrier are selected such that the excitation radiation imaged by the light source unit on the specimen carrier is reflected in such a way that essentially no excitation radiation reaches the detection beam path. However, the fluorescence measurement volume is not limited to a small section at the base of the sample container, for example a tissue culture dish or each well of a microtiter plate.

Hence, there remains a need for an improved apparatus and method for fluorescence measurements of substances in sample carriers, such as tissue culture dishes and microtiter plates, as typically used for adherent cell assays and homogeneous fluorescence assays which solves the problems of the previously discussed known systems. Such an improved apparatus and method desirably would be capable of:

imaging-based fluorescence measurement, as required for simultaneous measurement of fluorescence from a plurality of sample volumes as desirable for high throughput;

wide-field excitation, as required for imaging-based fluorescence measurement;

angular separation of the optical paths of incident and reflected excitation light from the optical path of fluorescence measurement, as desirable to suppress spectral leakage and/or minimize cost of spectral filtration; and limitation of the fluorescence measurement to a small volume selected at a depth in the sample carrier proximate to the optically transparent bottom member of the carrier, in order to render the fluorescence measurements immune to variability in total volume of solution and/or surface tension, to make the position of the fluorescence measurements insensitive to divergence of the excitation illumination, and to minimize the effects of fluorescent or autofluorescent supernatant, attenuation of both the excitation and emission radiation in the solution, and scattering-induced depolarization when the solution is turbid. It would further be desirable if only one excitation path were used to minimize cost and complexity of the apparatus.

SUMMARY OF THE INVENTION

An object of the present invention is to provide an apparatus and method for fluorescence measurements that will meet the needs previously discussed in this specification. Another object of the present invention is to lessen the severity of the problems of prior systems as previously discussed in this specification.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the claims.

An apparatus according to the invention is particularly useful for depth selected fluorescence measurements of a sample. The apparatus may include a carrier for at least one sample substance, the carrier having at least one transparent, planar bottom wall with an upper surface. Projection optics are provided that include a first optical axis, to expose the at least one sample substance through the bottom wall to a spatially structured pattern of excitation radiation, the projection optics also including a first object plane and an image plane that are subject to a Scheimpflug condition, the image plane being substantially coplanar with the upper surface of the bottom wall of the carrier. An image capture module is provided that includes a second optical axis, a second object plane substantially coplanar with the image plane, and a detection beam path, to receive a data image from the sample. A signal processor, such as a specially programmed computer, is provided to transform the data image to provide depth selected fluorescence measurement for the at least one sample substance. The apparatus also includes an arrangement whereby the first optical axis is inclined relative to the second optical axis so that the projection optics has an angle of inclination relative to the image plane, the angle of inclination being selected such that a component of excitation radiation incident upon, but not absorbed by, the at least one sample substance is scattered or reflected to substantially reduce excitation radiation from reaching the detection beam path.

The spatially structured pattern of excitation radiation used in the apparatus may have a periodicity in a direction perpendicular to a direction of a projection of the first optical axis onto the image plane, so that the phase of the structured pattern of excitation radiation does not change with increasing depth into an image space. The projection optics may include at least one non-telecentric Scheimpflug lens system which may be zoomable. Alternatively, the projection optics may include at least one Scheimpflug lens system providing object space telecentricity which may be zoomable. Or, the projection optics may include at least one Scheimpflug lens system providing image space telecentricity which may be zoomable. The carrier may be a microtiter plate having a plurality of wells for receiving sample substances, each well having a transparent, planar bottom wall.

A method according to the invention is useful for depth selected fluorescence measurements of a sample. The inventive method may include steps of providing a carrier for at least one sample substance, the carrier having at least one transparent, planar bottom wall having an upper surface; providing projection optics having a first optical axis, the projection optics including a first object plane and an image plane that are subject to a Scheimpflug condition, the image plane being substantially coplanar with the upper surface of the bottom wall of the carrier; providing an image capture module having a second optical axis, a second object plane substantially coplanar with the image plane, and a detection beam path; inclining the first optical axis relative to the second optical axis so that the projection optics has an angle of inclination relative to the image plane, the angle of inclination being selected such that a component of excitation radiation incident upon, but not absorbed by, the at least one sample substance is scattered or reflected to substantially reduce excitation radiation from reaching the detection beam path; exposing the at least one sample substance through the bottom wall to a spatially structured pattern of excitation from the projection optics; receiving a data image from the at least one sample following exposure to the spatially structured pattern, using the image capture module; and using a computer, transforming the data image to provide depth selected fluorescence measurement for the at least one sample substance. The samples substance may be turbid. The carrier of the method may be a microtiter plate having a plurality of wells for receiving sample substances, each well having a transparent, planar bottom wall. The structured pattern of excitation radiation may have a periodicity in a direction perpendicular to a direction of the projection of the first optical axis onto the image plane, so that the phase of the structured pattern of excitation radiation does not change with increasing depth into an image space.

BRIEF DESCRIPTION OF THE DRAWINGS

FIG. 14A shows a cross-sectional view along line 14-14 of the microtiter plate of FIGS. 1A and 1B when illuminated by the apparatus shown in FIG. 7.

FIG. 14B shows a detailed view of FIG. 14A.

DETAILED DESCRIPTION OF THE INVENTION

Figure 1A:
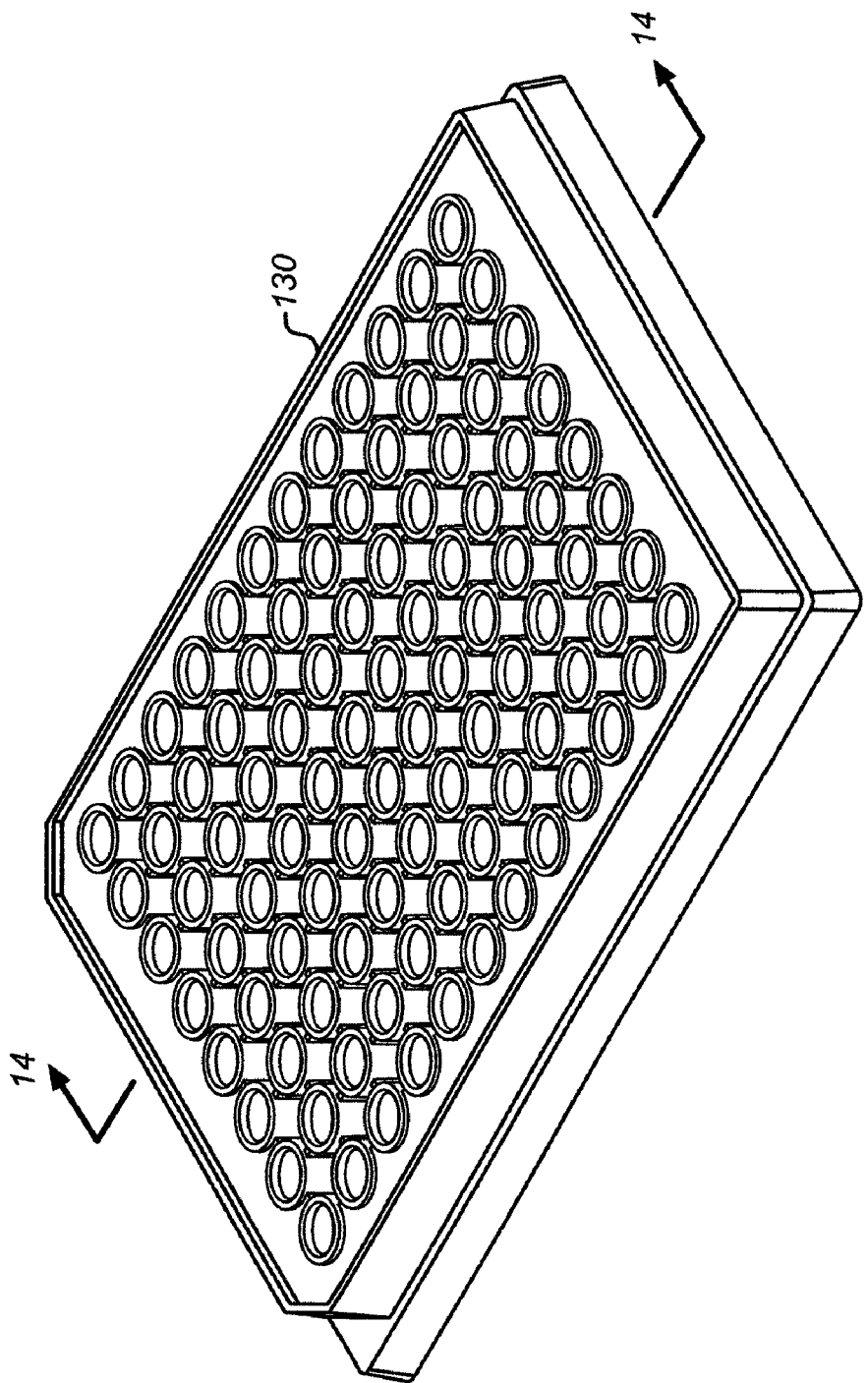
FIG. 1A shows a perspective view from above of a known type of 96 well microtiter plate, revealing the upper openings of its wells for introduction of sample substances.

The invention has been described in detail with particular reference to certain preferred embodiments thereof, but it will be understood that variations and modifications can be effected within the spirit and scope of the invention. The following is a detailed description of the preferred embodiments of the invention, reference being made to the drawings in which the same reference numerals identify the same elements of structure in each of the several figures.

Figure 6A:
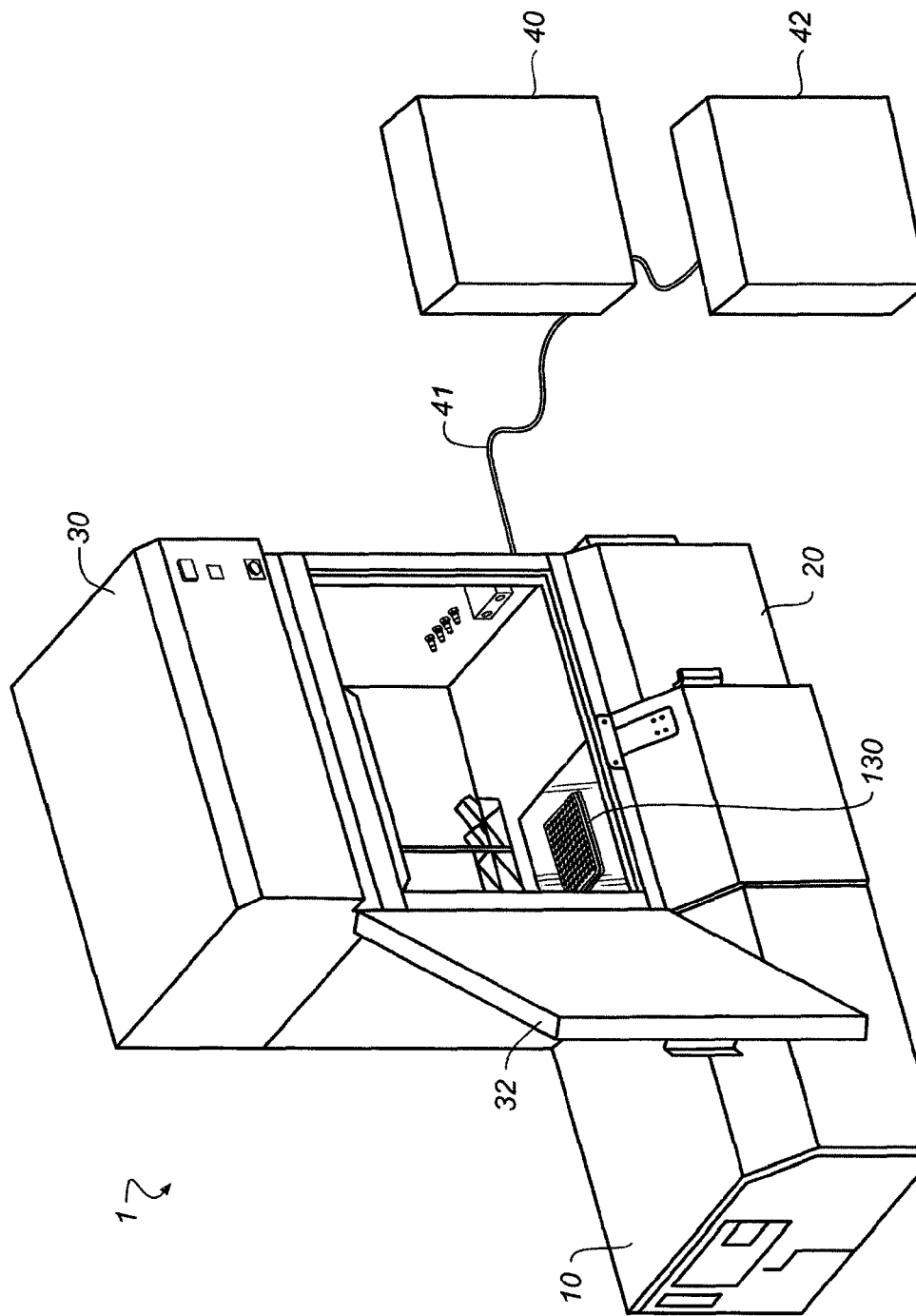
FIG. 6A shows a perspective view of an exemplary electronic imaging system suitable for use in accordance with the present invention.
Figure 6B:
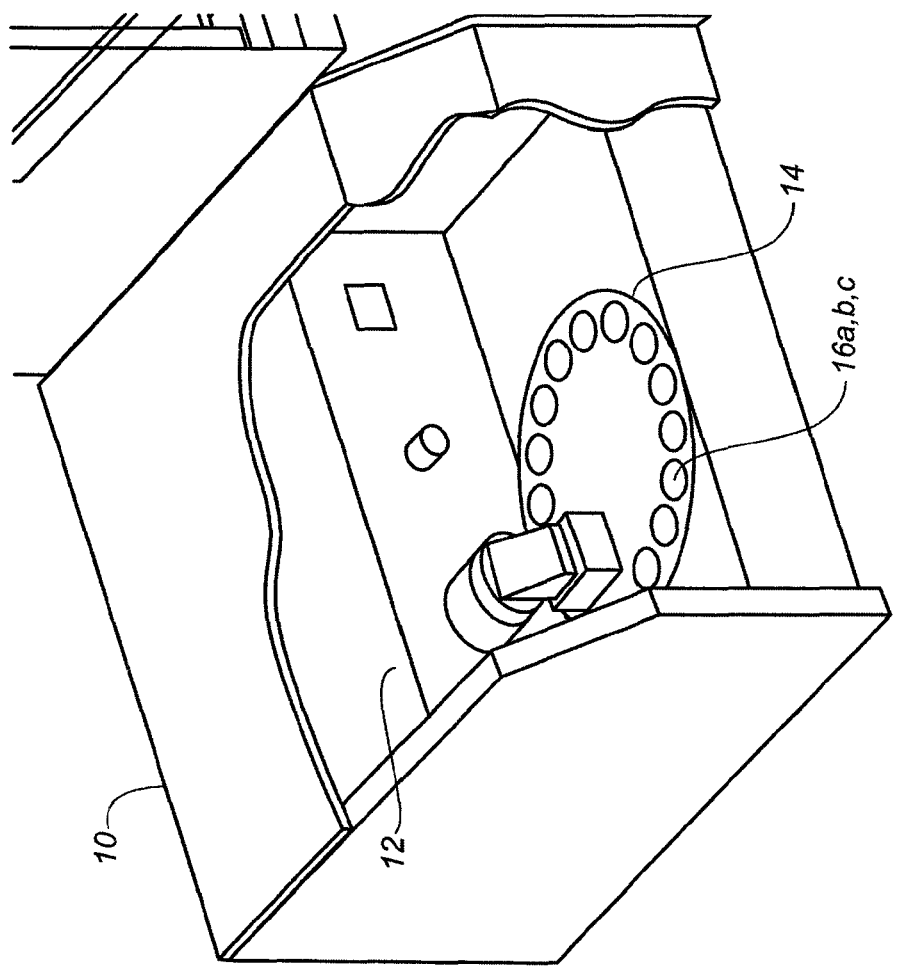
FIG. 6B shows a partially cutaway perspective view of the excitation radiation source of the imaging system of FIG. 6A.

FIG. 6A shows a perspective view of an exemplary electronic imaging system 1, suitable for use in accordance with the present invention. FIG. 6B shows a partially cutaway perspective view of the excitation radiation source of imaging system 1. Imaging system 1 includes an excitation radiation source 10 for fluorescence excitation, an image capture module 20 to receive the data image from a sample, a sample cabinet 30, and a communication and computer control system 40. Source 10 includes a lamp unit 12, for example a halogen or xenon lamp unit, and an excitation filter wheel 14 containing a plurality of excitation filters 16a, b, and c. Alternative excitation radiation sources known in the art include lamp sources employing an excitation filter slider, light emitting diode based sources, and laser sources. Source 10 is optically coupled to image capture module 20, for example by a randomized fiber optic bundle, not illustrated. Image capture module 20 is substantially optically sealed from ambient light. Sample cabinet 30 is also normally substantially optically sealed from ambient light, and includes a door 32, which is closed during image capture. Communication and computer control system 40 communicates with image capture module 20 via a communication cable 41, and can include a display device 42, for example, a computer monitor.

Figure 7:
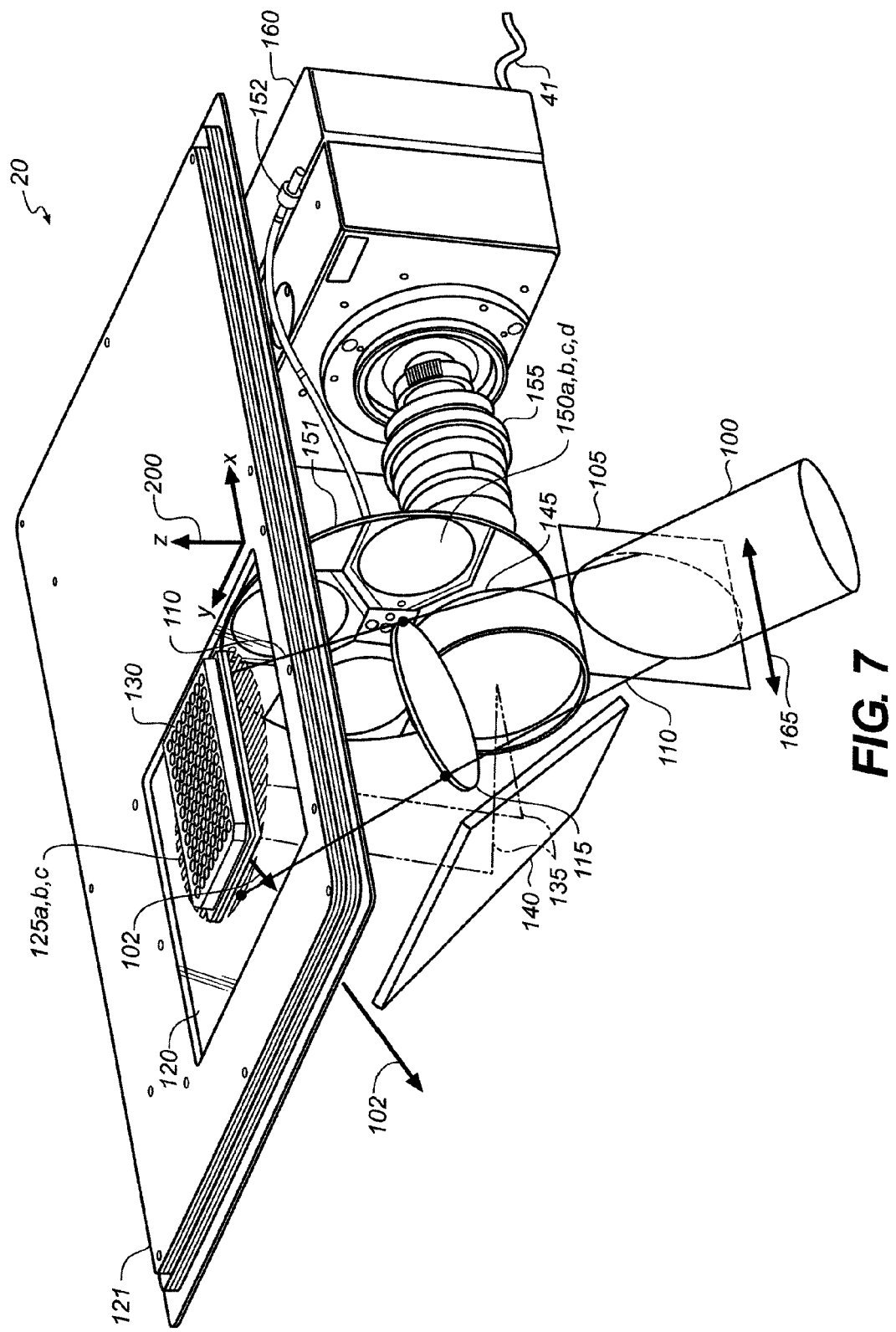
FIG. 7 shows a cutaway perspective view of components of the image capture module of the imaging system of FIG. 6A, suitable for use in accordance with a first embodiment of the present invention wherein spatially modulated excitation radiation is delivered using a non-telecentric Scheimpflug lens system.

FIG. 7 shows a cutaway perspective view of components of image capture module 20 suitable for use in accordance with a first embodiment of the present invention wherein spatially structured or modulated excitation radiation is delivered using projection optics including a non-telecentric Scheimpflug lens system 115. An X-Y-Z coordinate system 200 is defined for ease of illustration and description. Image capture module 20 delivers excitation radiation 100, which is optionally linearly polarized, via projection optics to an optically transparent platen 120, which is incorporated into an object stage 121. A sample carrier, such as a microtiter plate 130, may be positioned on platen 120. Alternatively, platen 120 may be omitted and carrier 130 may be supported on stage 121 above a suitable opening. Each well of plate 130 has an optically transparent, substantially planar bottom wall or member 132 having an upper surface immediately above which the fluorescent sample substance(s) is(are) disposed within the well. Typically, the range of thickness of wall 132 is in the range of 0.01 to 5.0 mm. Alternatively, other sample carriers known in the art may be used, such as tissue culture dishes having optically transparent, substantially planar bottom walls, not illustrated. Excitation radiation 100 is transmitted through a one-dimensional spatial modulation grid 105, further described with regard to FIG. 8. The spatial modulation grid is coplanar with the object plane of projection optics including a non-telecentric Scheimpflug lens system 115. In the embodiment shown, the non-telecentric Scheimpflug lens system includes a single lens group as indicated; however, generally more than one lens group may comprise a non-telecentric Scheimpflug lens system. The spatial modulation grid is configurable or movable to produce a plurality of phases that shift along the direction indicated by arrow 165. Image capture module 20 also includes a fluorescence detection system, wherein the fluorescence signal is imaged through a detection beam path 135 by a detection lens system including a detection lens 155 and a detection lens diopter 145, onto a sensor in a digital camera 160, such as a thermoelectrically cooled charge coupled device camera. A folding mirror 140 inserted in the detection beam path enables a compact layout of the image capture module. A plurality of emission filters 150a, b, c, and d in an emission filter wheel 151 provides spectral selection of the fluorescence signal using an actuator 152, as well as rejection of excitation radiation from the sensor. The fluorescence detection system optionally may include a linear polarizing optic, not shown, which is cross-polarized with respect to the optionally linearly polarized excitation radiation. Such a polarizing optic may be useful during fluorescence polarization analyses, as previously discussed. Those skilled in the art will appreciate that all of the wells of plate 130 simultaneously may be illuminated and their fluorescence detected by the apparatus of the invention. Alternatively, without departing from the scope of the invention, the wells may be illuminated section by section, such as quadrant by quadrant; and their fluorescence detected.

Lens system 115 delivers the spatially structured or modulated excitation radiation through a divergent beam path 110 to the top surface of the platen 120, i.e., the X-Y plane of stage 121. This top surface or plane preferably is substantially coplanar with (a) the image plane of lens system 115, (b) the upper surface of optically transparent bottom wall or member 132 of the sample carrier, and (c) the object plane of the fluorescence detection lens system 155, to within the smaller of the depths of focus of both the image plane of lens system 115 and the object plane of the fluorescence detection lens system 155.

By definition, a Scheimpflug lens system forms an image of an object whereby the object and image planes are not parallel to each other, but are instead inclined with respect to each other. The examples used throughout this specification show object and image planes (such as at grid 105 and top surface of platen 120, respectively) that are perpendicular with respect to each other. In general the inclination of the object and image planes can be any arbitrary angle, including obtuse angles if folding mirrors are used in the Scheimpflug lens system. Upon reaching the platen surface, the spatially structured or modulated excitation radiation 125a, b, and c, propagates further into the space beyond the platen, i.e., into the image space depth, which is the positive Z direction, wherever transmission of the sample carrier allows, e.g., through the substance in the wells in microtiter plate 130. The substance(s) in the sample carrier subtend(s) the image space with fluorescent material and provide(s) spatially distributed fluorescence signal(s) with spatial modulation in proportion to the spatially structured or modulated excitation radiation at the image plane of lens system 115. As illustrated, the projection optics are set at an angle relative to the image plane at the top surface of platen 120. This angle is selected so that the component of the excitation radiation from beam path 110 that is not absorbed by the substance(s) in the sample carrier, and also not absorbed by the sample carrier itself, is reflected and/or scattered predominantly along a direction indicated by the arrow 102. As a result, the unabsorbed excitation radiation is reflected and scattered away from detection beam path 135, thereby minimizing the potential for that excitation radiation to cause background in the fluorescence signal. Furthermore, because cost of the emission filters is increased and fluorescence transmission of the emission filters is decreased with increased rejection of the excitation radiation, the reflection of the excitation radiation away from the detection beam path enables low cost emission filtration with high transmission.

Figure 2A:
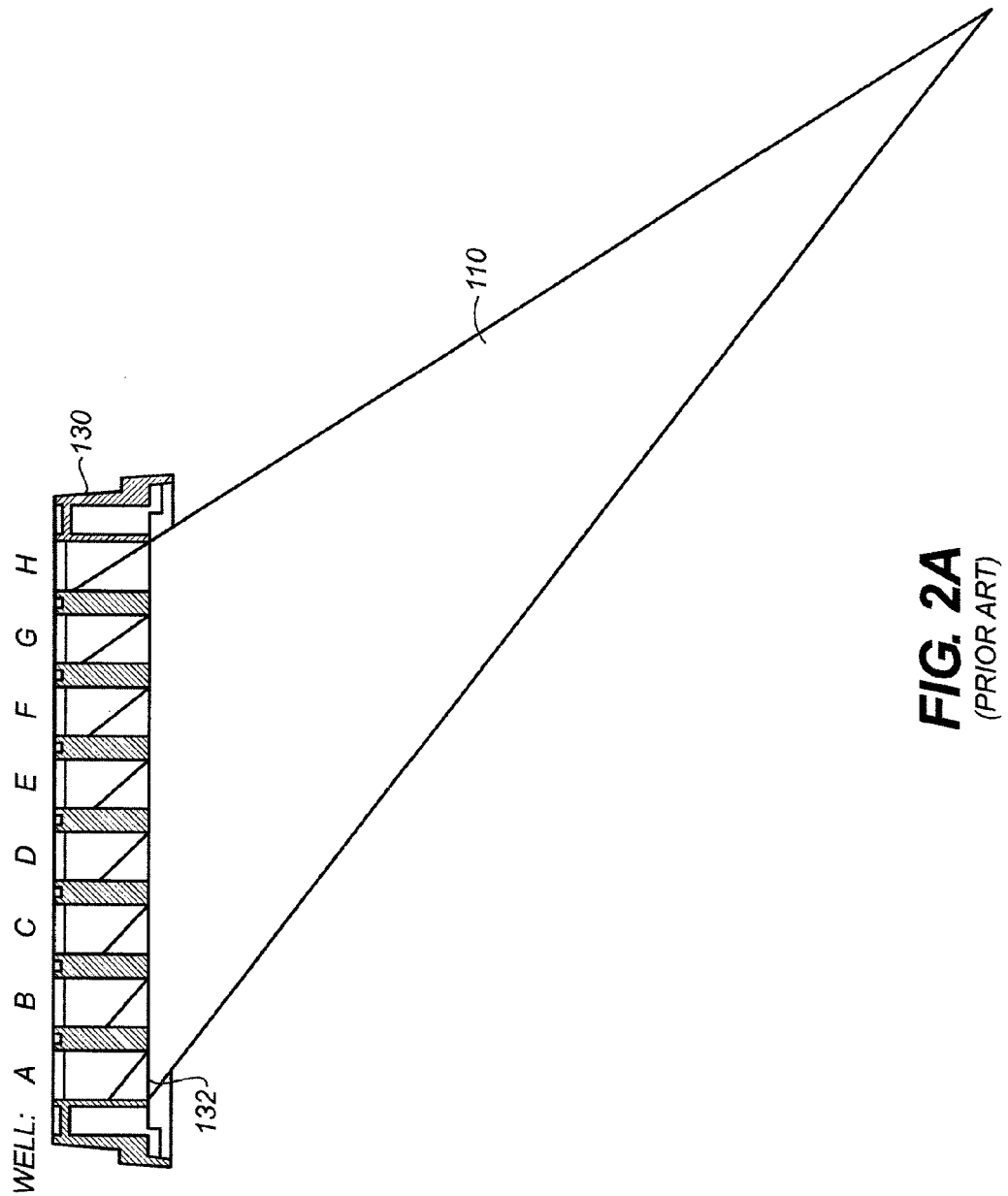
FIG. 2A shows how the microtiter plate of FIGS. 1A and 1B may be illuminated from below by a single divergent beam of radiation.
Figure 2B:
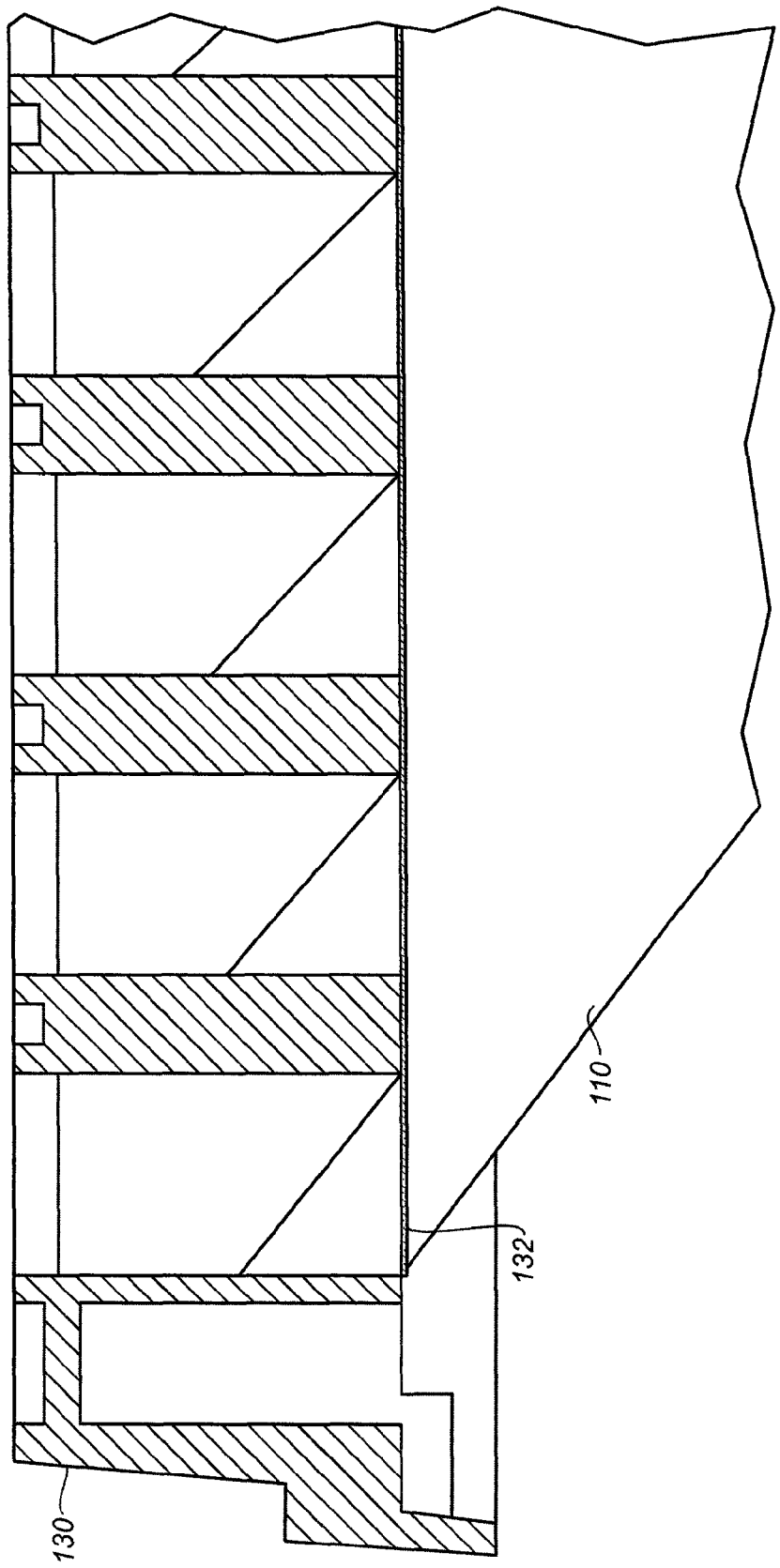
FIG. 2B shows an enlarged portion of FIG. 2A, indicating how different volumes of sample substance and supernatant liquid are excited by the radiation.
Figure 3:
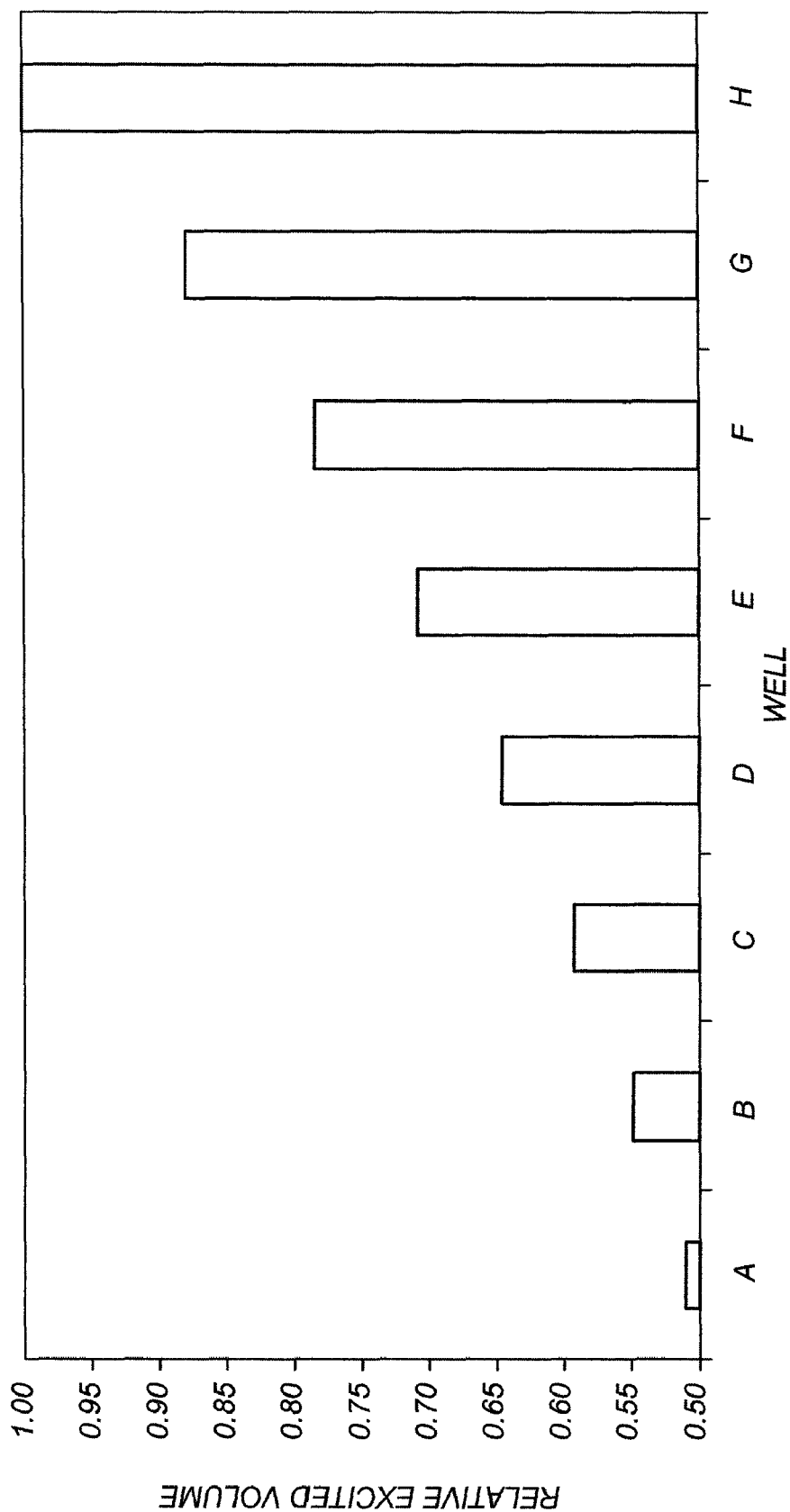
FIG. 3 shows the relative variations of excited volumes when illuminated as in FIG. 2A.
Figure 4:
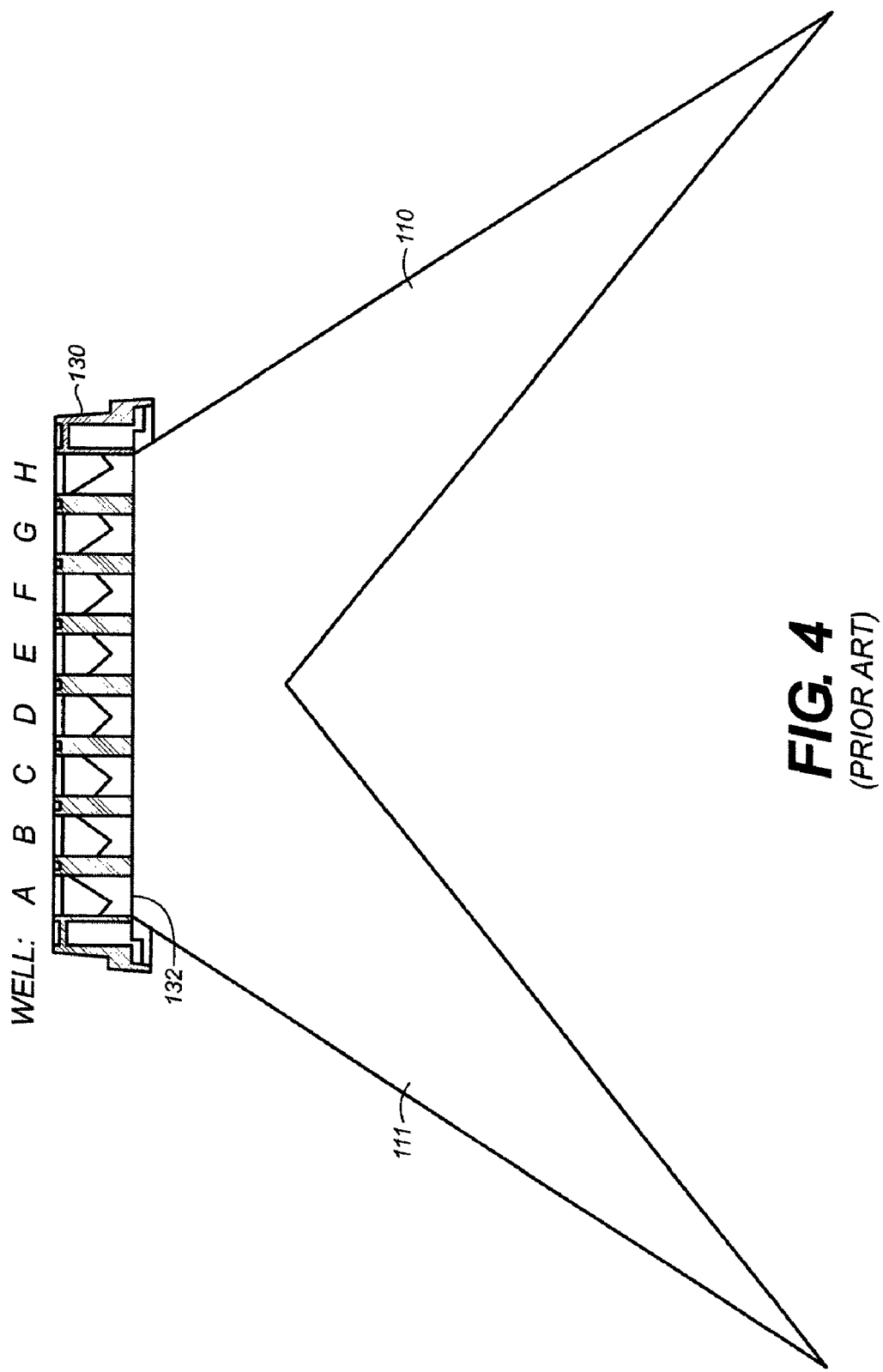
FIG. 4 shows how the microtiter plate of FIGS. 1A and 1B may be illuminated from below by a pair of symmetrically located divergent beams of radiation.
Figure 5:
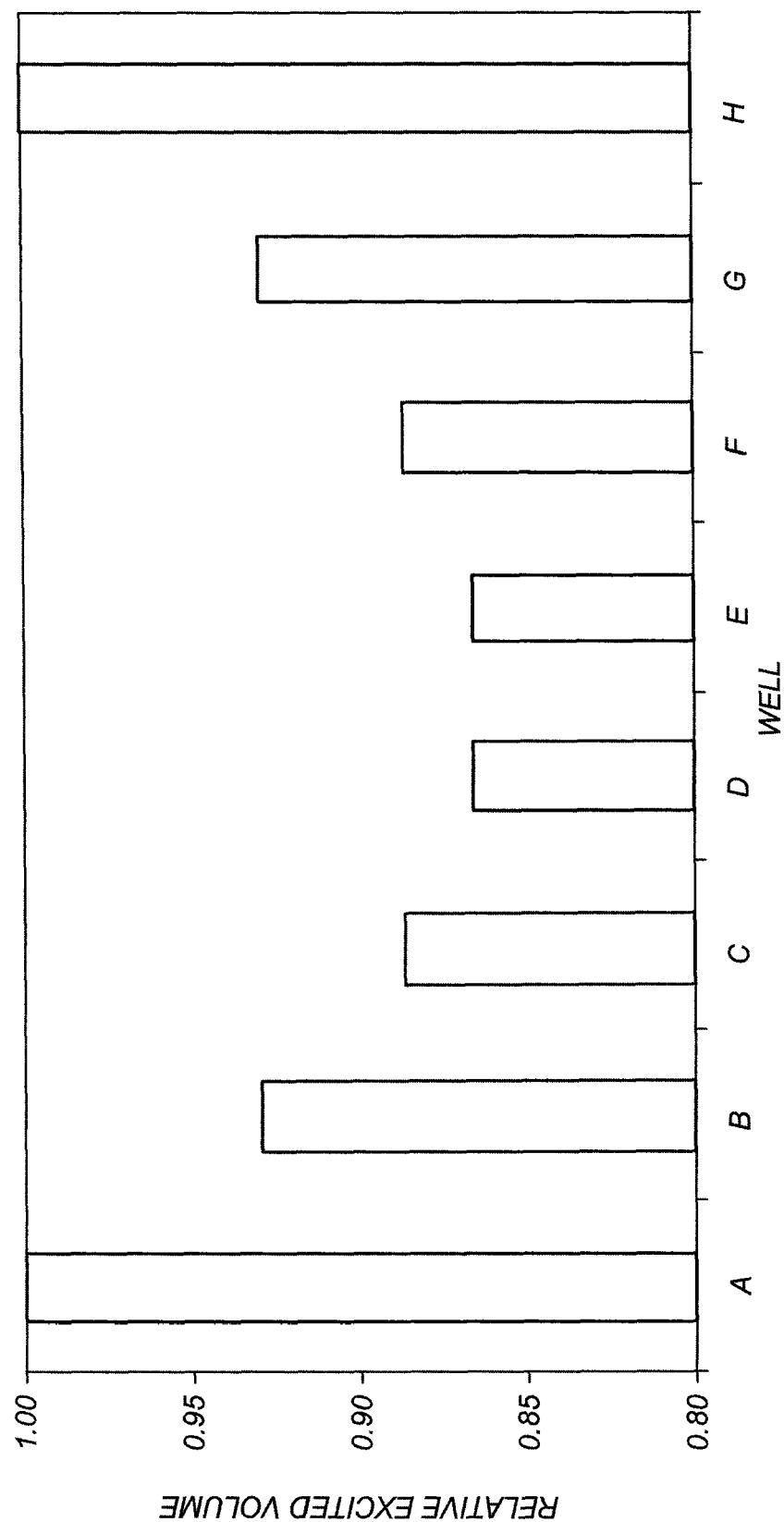
FIG. 5 shows the relative variations of excited volumes when illuminated as in FIG. 4.
Figure 8:
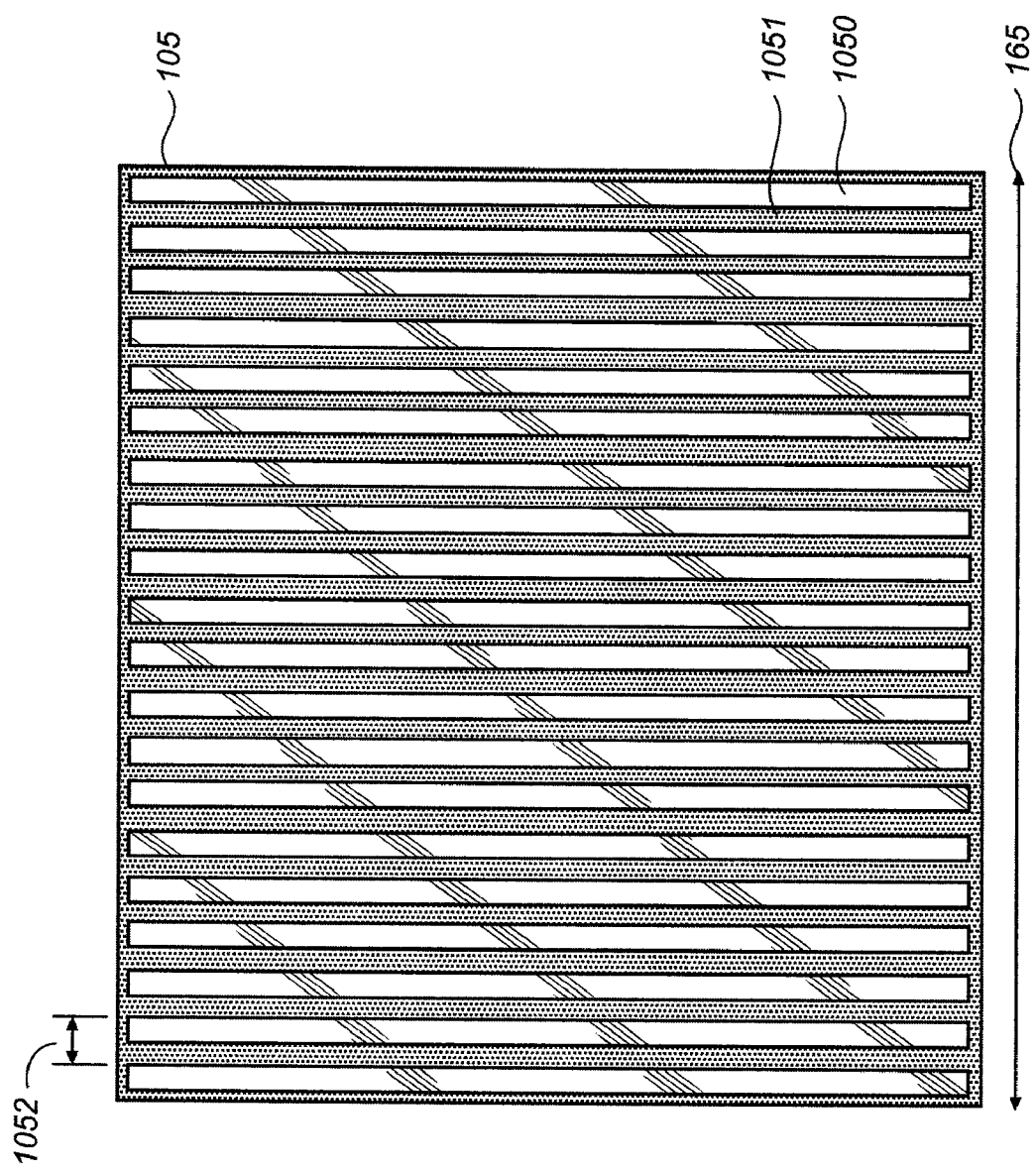
FIG. 8 shows a diagrammatic view of the spatial modulation grid used in the image capture module of FIG. 2.

FIG. 8 shows a diagrammatic view of spatial modulation grid 105 used in image capture module 20. In the embodiments described throughout, the spatial modulation grid includes an alternating periodic pattern of transparent and non-transparent stripes, 1050 and 1051, respectively. The spatial modulation grid is oriented so that the alternation of the periodic pattern of transparent and non-transparent stripes is along the direction shown by arrow 165 in FIGS. 2 and 3, i.e., parallel to the image plane, in this example the platen surface. Furthermore, the spatial modulation grid can be incrementally shifted or translated along the direction indicated by the arrow 165, by fractions of the spatial modulation period 1052. Such translation can be used to produce a plurality of phases of the spatial modulation corresponding to a plurality of fluorescence images comprising a fluorescence image set, whereby one phase of spatial modulation is selected for each fluorescence image in the fluorescence image set so as to perform depth selection. The translation of the spatial modulation grid may be achieved by a piezoelectronically driven actuator, not illustrated, wherein amplified voltage is applied to a piezoelectric crystal to change its length, thereby providing highly accurate repositioning of the grid pattern. The spatial modulation grid 105 may be formed by selective removal of material from a solid sheet of material, and may be simply a single grid with a given spatial modulation frequency. Alternatively, the spatial modulation grid may be an electronically programmable electro-optic matrix, for example a liquid crystal matrix or a digital micromirror matrix.

Figure 9:
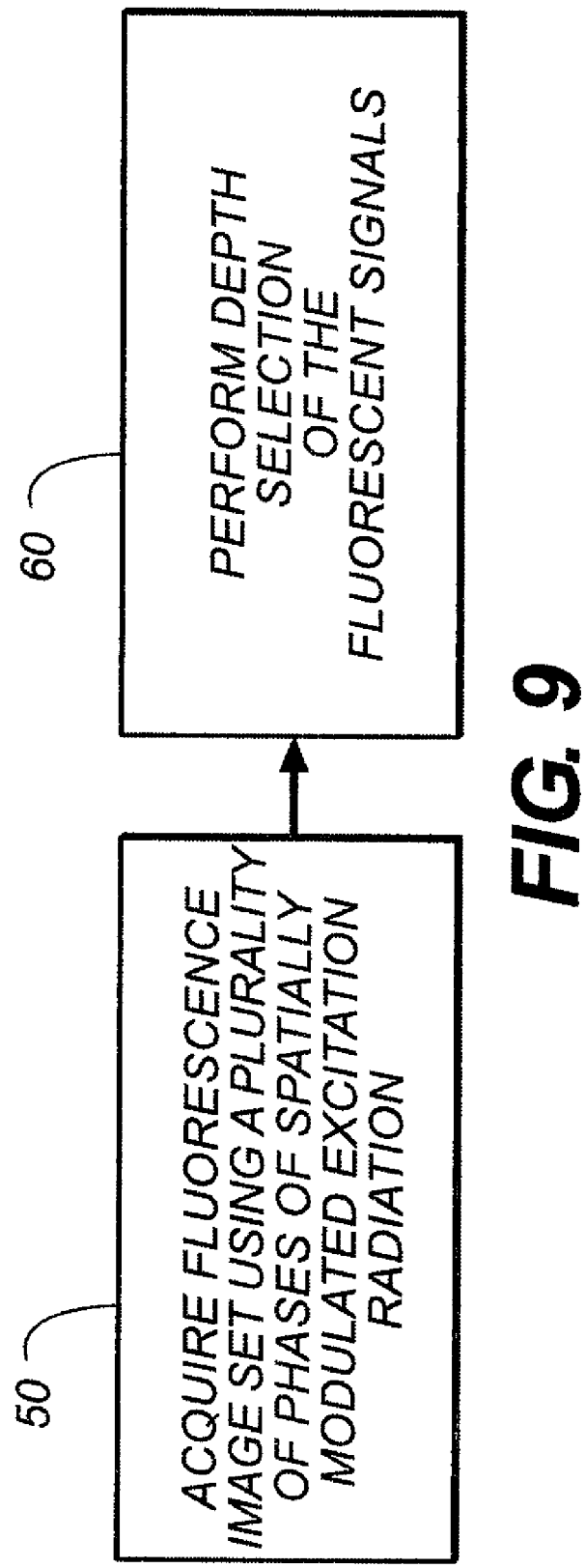
FIG. 9 shows a workflow diagram in accordance with a method of the present invention.

FIG. 9 shows a workflow diagram in accordance with a first method of the present invention. First, a fluorescence image set is acquired using a plurality of phases of spatially modulated excitation radiation, step 50. Second, depth selection of the fluorescent signals is performed, step 60. A depth selection within the wells of carrier 130 is performed by communication and computer control system 40 which includes a signal processor. The depth selection is achieved by computational algorithms known in the art, such as those disclosed in U.S. Pat. No. 6,376,818 or in German patent publication 199 30 816. In accordance with the invention, the depth selected preferably is just above the upper surface of bottom wall 132. This depth is considered to provide the benefit of reducing the severity of the problems of prior art systems as previously discussed. Those skilled in the art will appreciate, however, that the depth selected may be varied somewhat without departing from the scope of the invention, though less than optimal results may be achieved. By virtue of the substantial coplanarity of the image plane of lens system 115, the upper surface of the optically transparent bottom member 132 of the sample carrier 130, and the object plane of detection lens system 155, the depth selection provides for a fluorescence response corresponding to the component(s) of the fluorescent substance(s) proximate to the optically transparent bottom member of the sample carrier.

Figure 10:
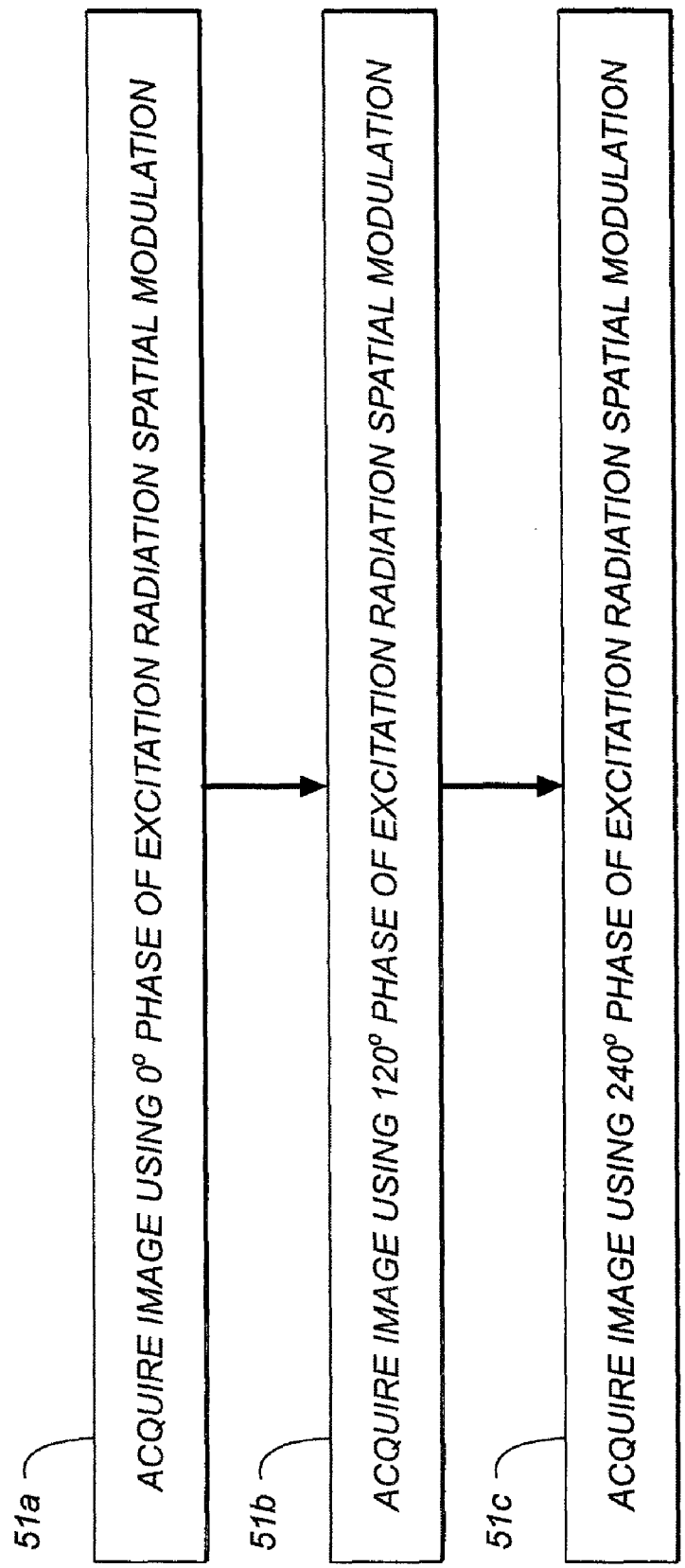
FIG. 10 shows a workflow diagram of an exemplary method used in step 50 of FIG. 9.
Figure 11A:
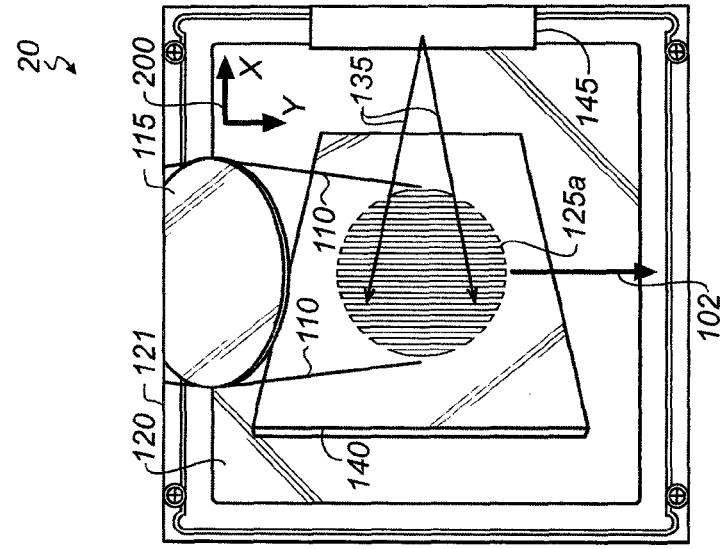
FIGS. 11a, 11b and 11c show cutaway diagrammatic views of the image capture module configured according to FIG. 7.
Figure 11B:
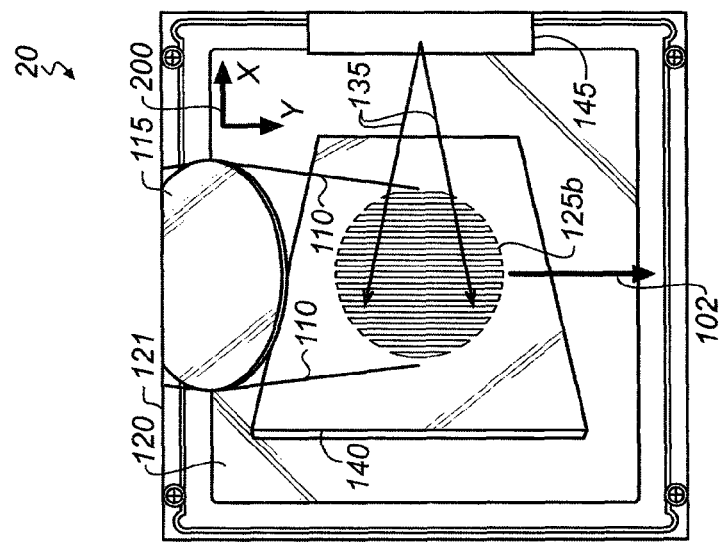
Figure 11C:
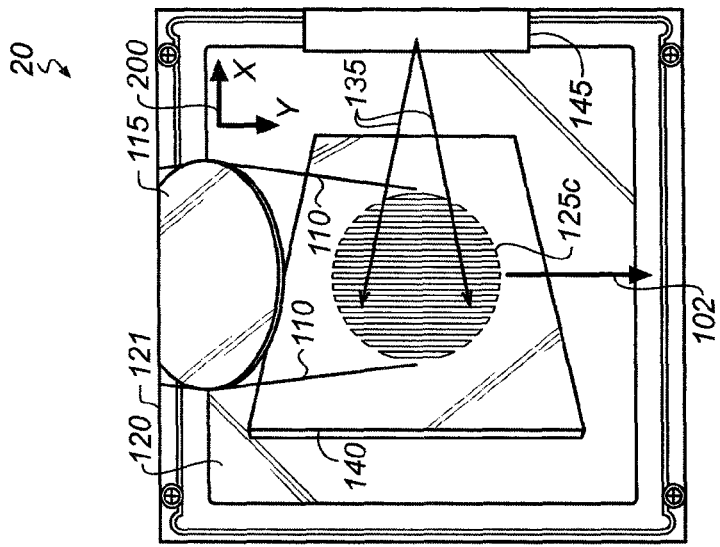
Figure 12:
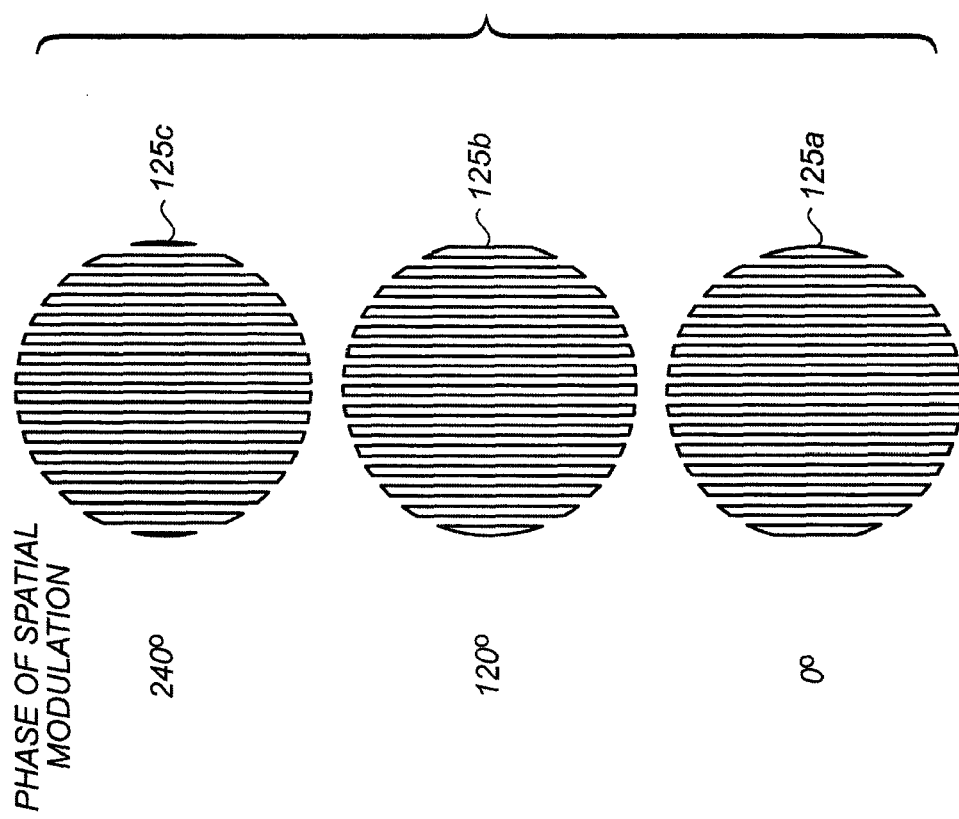
FIG. 12 shows diagrammatic views of the spatially modulated excitation radiation of FIGS. 11a, 11b and 11c.

FIG. 10 shows a workflow diagram of an exemplary method used in step 50 of FIG. 9 wherein the plurality of phases includes three relative phases, specifically 0 degrees step 51a, 120 degrees step 51b, and 240 degrees step 51c, i.e., one-third steps of the spatial modulation period length. FIGS. 11a, 11b and 11c show cutaway diagrammatic views of image capture module 20. The perspective of the view is from directly below platen 120. FIGS. 11a, 11b and 11c show the spatially structured or modulated excitation radiation 125a, b, and c, respectively, whereby the relative phase of the spatial modulation is 0 degrees, 120 degrees, and 240 degrees, respectively. An X-Y coordinate system 200 is shown for ease of illustration and discussion. FIG. 12 shows diagrammatic views of the spatially modulated excitation radiation of FIGS. 11a, 11b and 11c in the X-Y plane. The relative phase is shifted by 0 degrees, 120 degrees, and 240 degrees in 125a, b, and c, respectively.

Figure 13A:
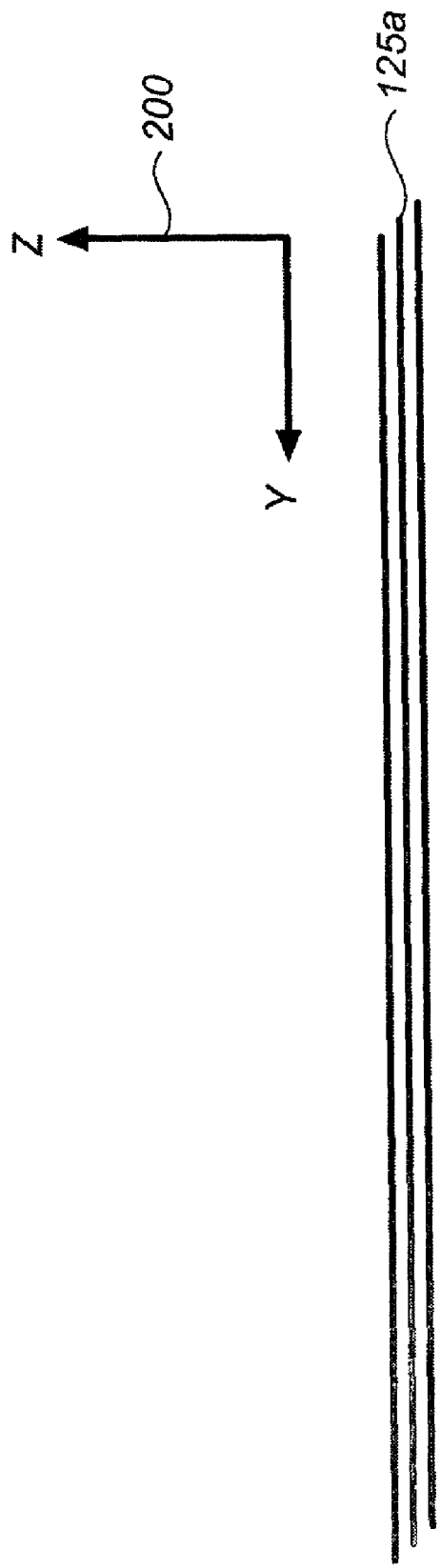
FIG. 13A shows a schematic of the spatially modulated excitation radiation patterns present at a series of planes, parallel to the X-Y image plane, distributed through the image space depth beyond the platen, i.e., in the positive Z direction.
Figure 13B:
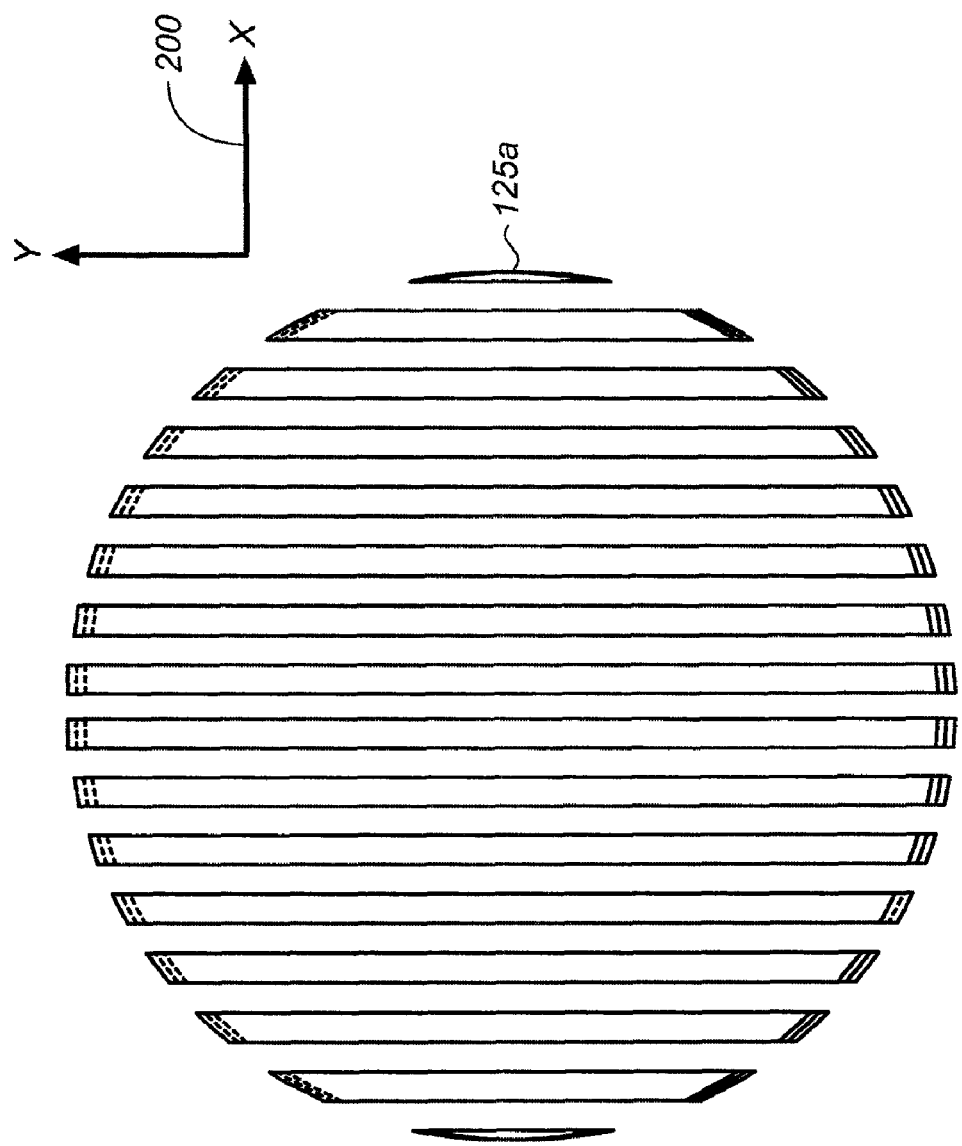
FIG. 13B shows a schematic of the spatially modulated excitation radiation patterns of FIG. 13A viewed from the Z direction.

FIG. 13A shows a schematic of the spatially modulated excitation radiation patterns present at a series of planes, parallel to the X-Y image plane, distributed through the image space depth beyond the platen, i.e., in the positive Z direction within the wells of carrier 130. FIG. 13B shows a schematic of the spatially modulated excitation radiation patterns of FIG. 13A viewed from the Z direction. In these schematics, the depth of modulation of the excitation radiation pattern decreases with increasing depth into the image space beyond the platen surface; i.e., the pattern is going out of focus. The schematics show that the spatially modulated excitation radiation pattern shifts in the positive Y direction, away from the object plane of the non-telecentric Scheimpflug lens system, with increasing depth into the image space beyond the platen surface. This shifting behavior is inherent to any Scheimpflug lens system and is due to lack of normality of the propagation vector of the excitation radiation with respect to the image plane. This shifting behavior restricts the orientation of the spatial modulation to be aligned with the X direction so that the phase of the spatial modulation does not change with increasing depth into the image space beyond the platen surface.

Figure 1B:
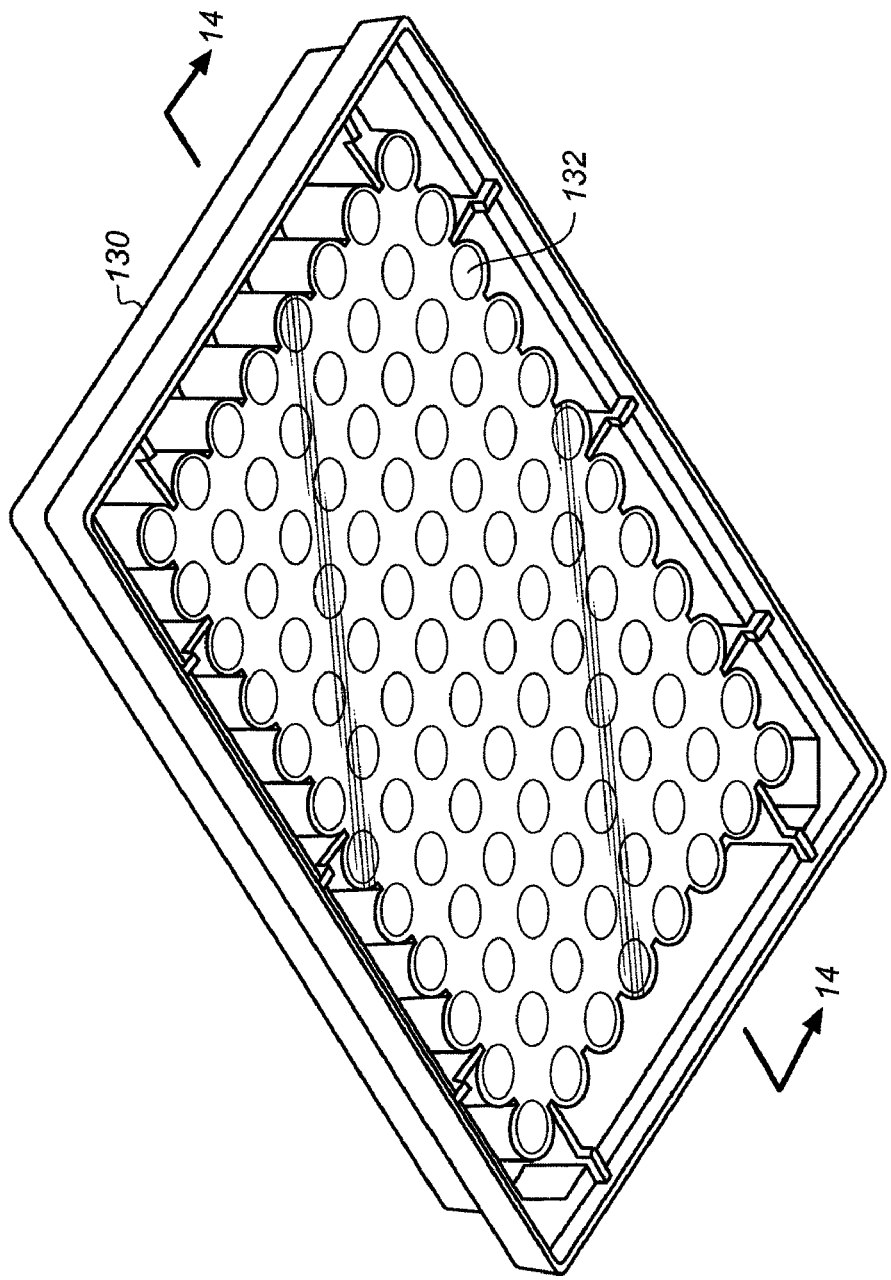
FIG. 1B shows a perspective view from below of the microtiter plate of FIG. 1A, revealing the planar optically transparent bottom walls of the sample wells.
Figure 15:
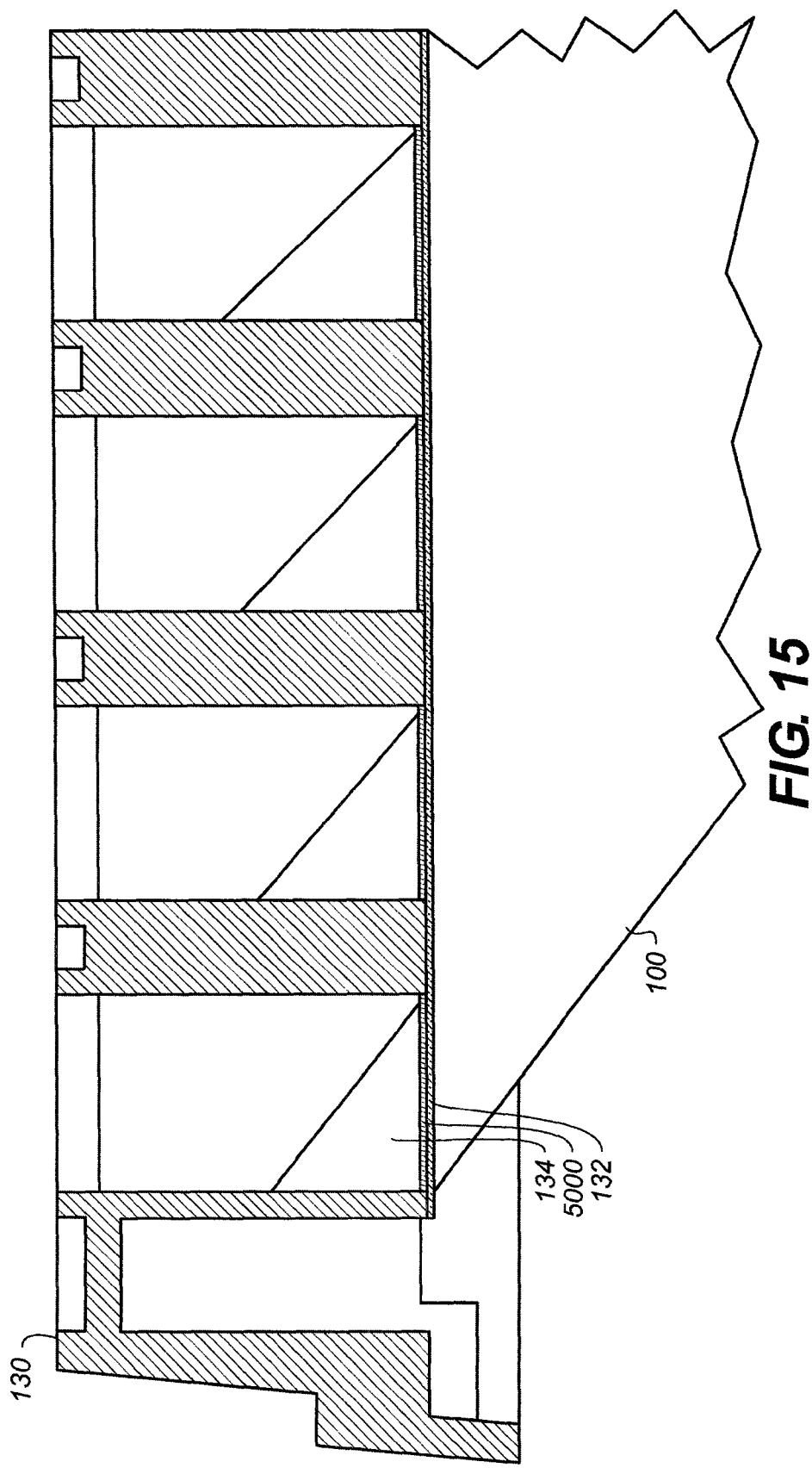
FIG. 15 shows a cross-sectional schematic orthogonal to FIGS. 14A and 14B.

FIG. 14A shows a cross-sectional schematic of the microtiter plate of FIGS. 1A and 1B, when illuminated by the apparatus shown in FIG. 7. FIG. 14B shows a detailed view of FIG. 14A. FIGS. 14A and 14B show that the spatially structured or modulated excitation radiation achieves greatest modulation (i.e., best focus) in a small section 134 proximate to the upper surface of optically transparent bottom member or wall 132 of the sample carrier 130. Hence the fluorescence detection volume is limited to section 134 by application of the depth selection achieved by the previously discussed computational algorithms. FIG. 15 shows a cross-sectional schematic orthogonal to FIGS. 14A and 14B. FIG. 15 shows that fluorescence detection volume 5000 is selected from the entire excited volume within each well of microtiter plate 130, and even though the entire excited volume within each well varies well-to-well, the fluorescence detection volume does not.

Figure 16:
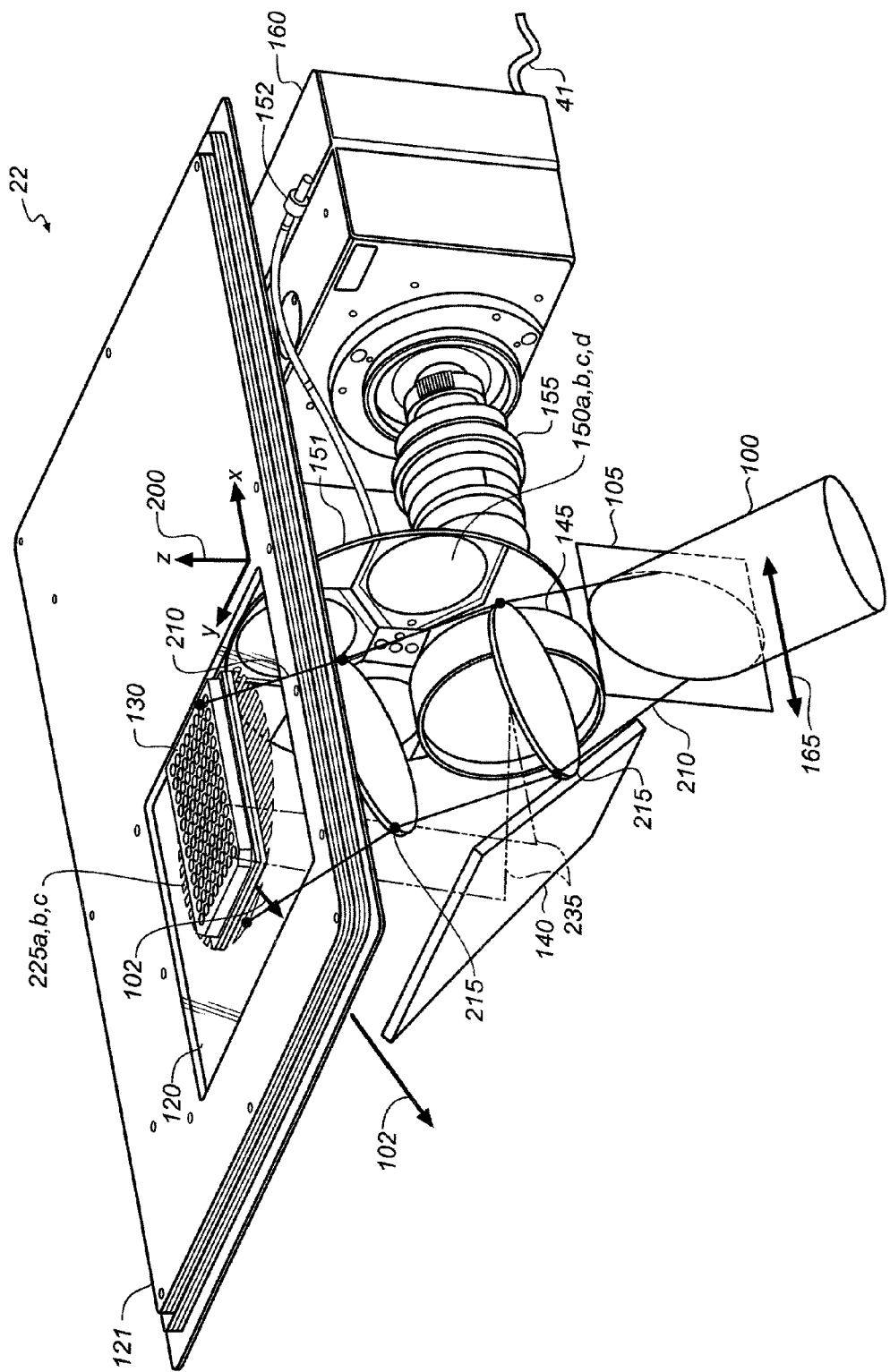
FIG. 16 shows a cutaway perspective view of components of the image capture module of the imaging system of FIG. 6A suitable for use in accordance with a second embodiment of the present invention wherein spatially modulated excitation radiation is delivered using a doubly telecentric Scheimpflug lens system.

FIG. 16 shows a cutaway perspective view of components of the image capture module 22 of the imaging system 1 in accordance with a second arrangement useful in accordance with the present invention wherein spatially structured or modulated excitation radiation is delivered using projection optics including a doubly telecentric Scheimpflug lens system 215. This embodiment is similar to the embodiment shown in FIG. 7, except the non-telecentric Scheimpflug lens system 115 has been replaced with the doubly telecentric Scheimpflug lens system 215. In the embodiment shown, the doubly telecentric Scheimpflug lens system includes two lens groups as indicated; however, generally more than two lens groups may comprise a doubly telecentric Scheimpflug lens system. By "doubly telecentric", it is meant that the lens system provides both object space telecentricity and image space telecentricity. The lens system delivers the spatially modulated excitation radiation through a beam path 210 to the surface of the platen 120 located at the image plane of the lens system, i.e., the X-Y plane. Upon reaching the platen surface, the spatially modulated excitation radiation 225a, b, and c, propagates further into the space beyond the platen, i.e., into the image space depth, which is the positive Z direction. The image space of the excitation Scheimpflug lens system is the object space of the fluorescence detection lens system, whereby the fluorescence signal is imaged through a beam path 235 by the detection lens system described previously. The excitation radiation is reflected along a direction indicated by the arrow 102; therefore, the excitation radiation is reflected away from the detection beam path, thereby minimizing the potential for that excitation radiation to cause background in the fluorescence signal.

Figure 17:
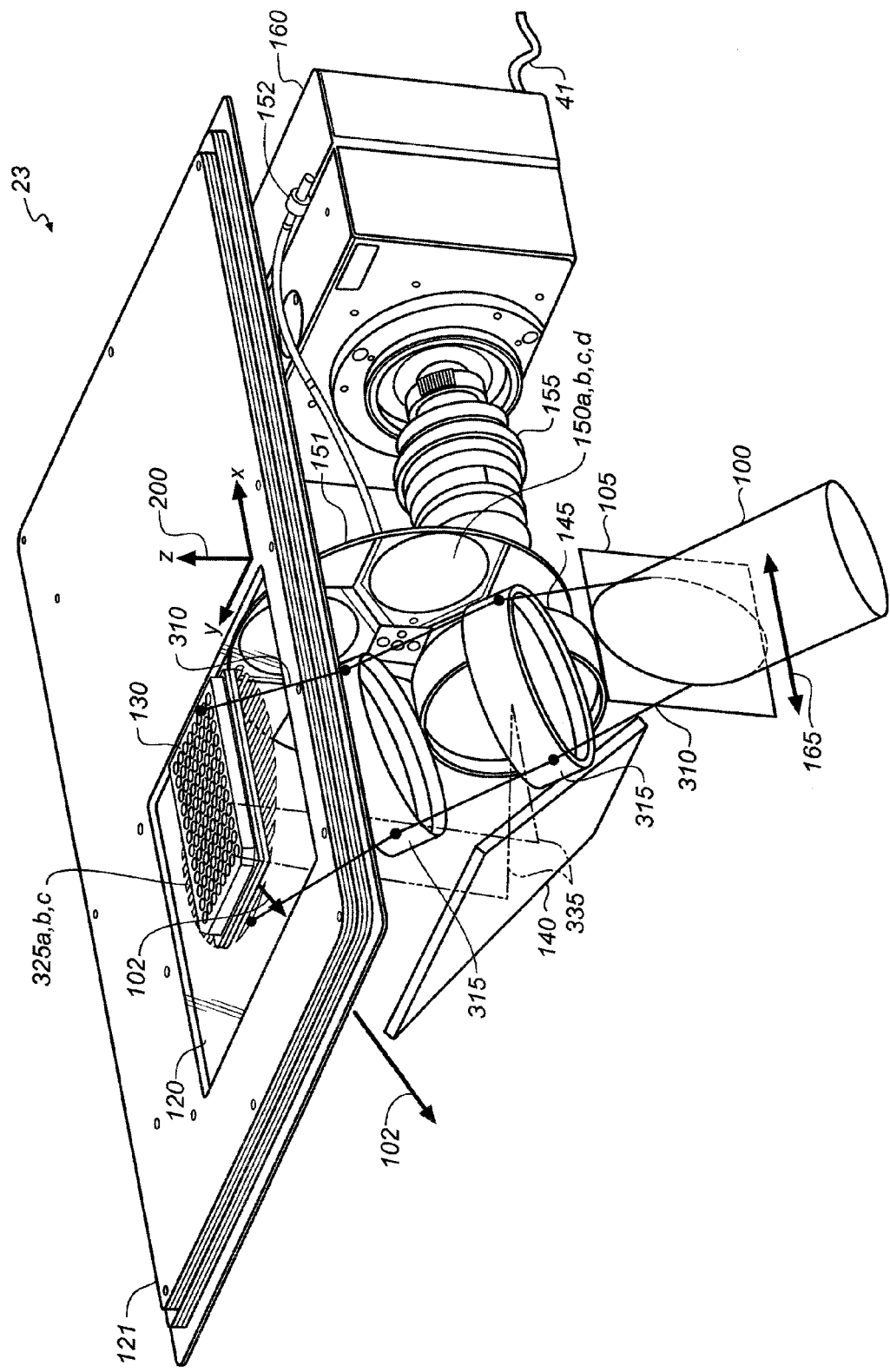
FIG. 17 shows a cutaway perspective view of components of the image capture module of the imaging system of FIG. 6A suitable for use in accordance with a third embodiment of the present invention wherein spatially modulated excitation radiation is delivered using a telecentric Scheimpflug zoom lens system.

FIG. 17 shows a cutaway perspective view of components of the image capture module 23 of the imaging system 1 in accordance with a third arrangement useful in accordance with the present invention wherein spatially modulated excitation radiation is delivered using projection optics including a doubly telecentric Scheimpflug zoom lens system 315 configured for high magnification. This embodiment is similar to the embodiment shown in FIG. 16, except the doubly telecentric Scheimpflug lens systems 215 has been replaced with the doubly telecentric Scheimpflug zoom lens systems 315. In the embodiment shown, the doubly telecentric Scheimpflug zoom lens system includes two lens groups as indicated; however, generally more than two lens groups may comprise a doubly telecentric Scheimpflug zoom lens system. One of ordinary skill in the art will understand that a plurality of doubly-telecentric fixed-focal lens systems providing different magnifications would provide equivalent benefits as a doubly telecentric zoom lens system. The lens system delivers the spatially modulated excitation radiation through a beam path 310 to the surface of the platen 120 located at the image plane of the lens system, i.e., the X-Y plane. Upon reaching the platen surface, the spatially modulated excitation radiation 325a, b, and c, propagates further into the space beyond the platen, i.e., into the image space depth, which is the positive Z direction. The image space of the excitation Scheimpflug lens system is the object space of the fluorescence detection lens system, whereby the fluorescence signal is imaged through a beam path 335 by the detection lens system described previously. The excitation radiation is reflected along a direction indicated by the arrow 102; therefore, the excitation radiation is reflected away from the detection beam path, thereby minimizing the potential for that excitation radiation to cause background in the fluorescence signal.

PARTS LIST 1 exemplary electronic imaging system
10 excitation radiation source
12 lamp unit
14 excitation filter wheel
16a, b, c excitation filters
20 image capture module
22 image capture module
23 image capture module
30 sample cabinet
32 door
40 communications and computer control system
41 communication cable 42 display device or monitor
50 step
51a, b, c step
60 step
100 excitation radiation
102 direction of reflection of excitation radiation
105 spatial modulation grid
110, 111 divergent beam path of spatially modulated excitation radiation
115 non-telecentric Scheimpflug lens system
120 optically transparent platen
121 object stage
125a, b, c spatially modulated excitation radiation pattern
130 96 well microtiter plate or sample carrier
132 bottom wall or member
134 section of best focus
135 detection beam path
140 folding mirror
145 detection lens diopter
150a, b, c, d emission filters
151 emission filter wheel
152 emission filter wheel actuator
155 detection lens
160 digital camera
165 direction to produce spatial phase shift
200 X-Y-Z coordinate system
210 beam path of spatially modulated excitation radiation
215 doubly telecentric Scheimpflug lens system
225a, b, c spatially modulated excitation radiation pattern
235 beam path of fluorescence detection
310 beam path of spatially modulated excitation radiation
315 doubly telecentric Scheimpflug zooming lens system
325a, b, c spatially modulated excitation radiation pattern
335 beam path of fluorescence detection
1050 transparent stripes
1051 non-transparent stripes
1052 spatial modulation period
5000 fluorescence detection volume

What is claimed is:

1. An apparatus for depth selected fluorescence measurements of a sample, the apparatus comprising:
   a carrier for at least one sample substance, the carrier having at least one transparent, planar bottom wall having an upper surface;
   projection optics having a first optical axis, to expose the at least one sample substance through the bottom wall to a spatially structured pattern of excitation radiation, the projection optics including a first object plane and an image plane that are subject to a Scheimpflug condition, the image plane being substantially coplanar with the upper surface of the bottom wall of the carrier;
   an image capture module having a second optical axis, a second object plane substantially coplanar with the image plane, and a detection beam path, to receive a data image from the sample;
   a signal processor to transform the data image to provide depth selected fluorescence measurement for the at least one sample substance; and
   an arrangement whereby the first optical axis is inclined relative to the second optical axis so that the projection optics has an angle of inclination relative to the image plane, the angle of inclination being selected such that a component of excitation radiation incident upon, but not absorbed by, the at least one sample substance is scattered or reflected to substantially reduce excitation radiation from reaching the detection beam path.

2. The apparatus of claim 1, wherein the projection optics comprise at least one non-telecentric Scheimpflug lens system.

3. The apparatus of claim 2, wherein the at least one non-telecentric Scheimpflug lens system is zoomable.

4. The apparatus of claim 1, wherein the projection optics comprise at least one Scheimpflug lens system providing object space telecentricity.

5. The apparatus of claim 4, wherein the at least one telecentric Scheimpflug lens system is zoomable.

6. The apparatus of claim 1, wherein the projection optics comprise at least one Scheimpflug lens system providing image space telecentricity.

7. The apparatus of claim 6, wherein the at least one Scheimpflug lens system is zoomable.

8. The apparatus of claim 1, wherein the carrier is a microtiter plate having a plurality of wells for receiving sample substances, each well having a transparent, planar bottom wall.

9. A method for depth selected fluorescence measurements of a sample, the method comprising steps of:
   providing a carrier for at least one sample substance, the carrier having at least one transparent, planar bottom wall having an upper surface;
   providing projection optics having a first optical axis, the projection optics including a first object plane and an image plane that are subject to a Scheimpflug condition, the image plane being substantially coplanar with the upper surface of the bottom wall of the carrier;
   providing an image capture module having a second optical axis, a second object plane substantially coplanar with the image plane, and a detection beam path;
   inclining the first optical axis relative to the second optical axis so that the projection optics has an angle of inclination relative to the image plane, the angle of inclination being selected such that a component of excitation radiation incident upon, but not absorbed by, the at least one sample substance is scattered or reflected to substantially reduce excitation radiation from reaching the detection beam path;
   exposing the at least one sample substance through the bottom wall to a structured pattern of excitation from the projection optics;
   receiving a data image from the at least one sample following exposure to the structured pattern, using the image capture module; and
   using a computer, transforming the data image to provide depth selected fluorescence measurement for the at least one sample substance in a detection volume proximate the upper surface of the bottom wall of the carrier.

10. The method of claim 9, wherein the sample substance is turbid.

11. The method of claim 9, wherein the carrier is a microtiter plate having a plurality of wells for receiving sample substances, each well having a transparent, planar bottom wall.

12. The method of claim 9, wherein the structured pattern of excitation radiation has a periodicity in a direction perpendicular to a direction of the projection of the first optical axis onto the image plane, so that the phase of the structured pattern of excitation radiation does not change with increasing depth into an image space.

13. The method of claim 12, wherein the sample substance is turbid.

14. An apparatus for depth selected fluorescence measurements of a sample, the apparatus comprising:

a carrier for at least one sample substance, the carrier having at least one transparent, planar bottom wall having an upper surface;

projection optics having a first optical axis, to expose the at least one sample substance through the bottom wall to a spatially structured pattern of excitation radiation, the projection optics including a first object plane and an image plane that are subject to a Scheimpflug condition, the image plane being substantially coplanar with the upper surface of the bottom wall of the carrier, wherein the structured pattern of excitation radiation has a periodicity in a direction perpendicular to a direction of a projection of the first optical axis onto the image plane, so that the phase of the structured pattern of excitation radiation does not change with increasing depth into an image space;

an image capture module having a second optical axis, a second object plane substantially coplanar with the image plane, and a detection beam path, to receive a data image from the sample;

a signal processor to transform the data image to provide depth selected fluorescence measurement for the at least one sample substance; and an arrangement whereby the first optical axis is inclined relative to the second optical axis so that the projection optics has an angle of inclination relative to the image plane, the angle of inclination being selected such that a component of excitation radiation incident upon, but not absorbed by, the at least one sample substance is scattered or reflected to substantially reduce excitation radiation from reaching the detection beam path.

* * * * *